United States Patent
Gulli et al.

(10) Patent No.: US 10,324,017 B2
(45) Date of Patent: Jun. 18, 2019

(54) LOCAL EFFECTIVE PERMEABILITY MEASUREMENTS FOR COMPLEX POROUS STRUCTURES

(71) Applicants: Stefano Gulli, Lewisville, TX (US); Luca Maddalena, Kennedale, TX (US)

(72) Inventors: Stefano Gulli, Lewisville, TX (US); Luca Maddalena, Kennedale, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 15/262,131

(22) Filed: Sep. 12, 2016

(65) Prior Publication Data
US 2017/0074773 A1 Mar. 16, 2017

Related U.S. Application Data
(60) Provisional application No. 62/217,822, filed on Sep. 12, 2015.

(51) Int. Cl.
*G01N 15/08* (2006.01)
(52) U.S. Cl.
CPC ....... *G01N 15/0826* (2013.01); *G01N 15/088* (2013.01); *G01N 2015/0846* (2013.01)
(58) Field of Classification Search
CPC combination set(s) only.
See application file for complete search history.

(56) References Cited

U.S. PATENT DOCUMENTS

| | | | | | |
|---|---|---|---|---|---|
| 4,769,606 | A | * | 9/1988 | Vinegar | G01V 3/24 250/256 |
| 5,387,865 | A | * | 2/1995 | Jerosch-Herold | G01N 15/08 324/300 |
| 5,503,001 | A | * | 4/1996 | Wong | G01N 33/241 324/351 |
| 2002/0189325 | A1 | * | 12/2002 | Bowen | G01N 15/08 73/38 |
| 2003/0136180 | A1 | * | 7/2003 | Garfinkle | G01N 15/0826 73/38 |
| 2005/0235757 | A1 | * | 10/2005 | De Jonge | G01F 1/704 73/861.07 |
| 2013/0003049 | A1 | * | 1/2013 | Matula | G01N 15/1459 356/72 |

OTHER PUBLICATIONS

Gulli, S., and L. Maddalena, "Characterization of Complex Porous Structures for Reusable Thermal Protection Systems: Effective-Permeability Measurements." Journal of Spacecraft and Rockets. (2014).
(Continued)

*Primary Examiner* — Clayton E. LaBalle
*Assistant Examiner* — Warren K Fenwick
(74) *Attorney, Agent, or Firm* — Thomas | Horstemeyer, LLP

(57) ABSTRACT

Disclosed are various embodiments for measuring a local permeability of a porous material. A probe can be positioned perpendicular to the surface of the material. The probe can be configured to sense a velocity of a fluid flowing over the surface. The probe can be positioned at a distance determined based on an average porosity of the material. The probe can take measurements at various positions at the distance by moving a minimum dimension between each measurement.

20 Claims, 31 Drawing Sheets

(56) References Cited

OTHER PUBLICATIONS

Gulli, S. et al., "Permeability Measurements of Complex Porous Structures for Reusable Thermal Protection Systems." 19th AIAA International Space Planes and Hypersonic Systems and Technologies Conference. (2014).
Gulli, S. et al., "Characterization of Complex Porous Structures for Reusable Thermal Protection Systems: Porosity Measurements." Journal of Spacecraft and Rockets (2015).
"Standard Test Method for Measurement of the Permeability of Unsaturated Porous Materials by Flowing Air," American Society for Testing and Materials Paper ASTM-D6539-13. Date: Unknown.
Zolutukhin, A.B. et al., Introduction to Petroleum Reservoir Engineering, Chapter 5, Picket Engelska, 2000. Date: Unknown.
Innocentini, M.D.M. et al., "Influence of Sample Thickness and Measurement Set-up on the Experimental Evaluation of Permeability of Metallic Foams," Journal of Porous Materials, vol. 17, No. 4, 2019, pp. 491-499. Date: Unknown.
Lomov, S.V. et al., "Permeability and Compressibility of CNT/CNF-Grafted Reinforcements," 10th International Conference on Flow Processes in Composite Materials, Jul. 2010.
Buntain, M.J. et al., "Compression Flow Permeability Measurements: A Continuous Technique," Journal of Composites: Part A, vol. 34, 2013, pp. 445-457. Date: Unknown.

* cited by examiner

LOCAL EFFECTIVE PERMEABILITY MEASUREMENTS FOR COMPLEX POROUS STRUCTURES

CROSS-REFERENCE TO RELATED APPLICATIONS

This application claims the benefit of U.S. Provisional Application No. 62/217,822, filed Sep. 12, 2015, the entire contents of which is hereby incorporated herein by reference.

BACKGROUND

Reusable thermal protection is a technology used to enable long duration hypersonic flights. Transpiration cooling has been demonstrated to be a promising active cooling technique in terms of coolant mass requirements and disturbance of the external flow. A methodology for the non-intrusive characterization of the local effective permeability of a complex carbon-carbon porous structure is described herein. The concept of effective permeability, which can be considered as the local blowing capability of a porous structure with respect to a selected coolant fluid, is also discussed. Specifically, the coolant (air) mass flux blown from a conical porous surface can be measured by a hot-film probe at a distance specified by an appropriate reference elementary area and the Reynolds number based on the diameter of the channels.

These measurements can be related to the pressure gradient across the local thickness of the material by using Darcy's law. Measurements can reveal a higher effective permeability near the nose of the cone where two longitudinal delaminations are identified. In one embodiment, the asymmetric blowing capability of the cone highlights an importance of characterizing the entire thermal protection system when contrasted with defining the overall properties of the material, which can be different at the full-scale level due to the geometry, the system integration (i.e. structural constraints), and the intrinsic defectology coming from the manufacturing process. In one example, the mass fluxes measured on the external porous surface supported the numerical aerothermal rebuilding of a wind-tunnel experiment on a transpiration cooling.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1A:
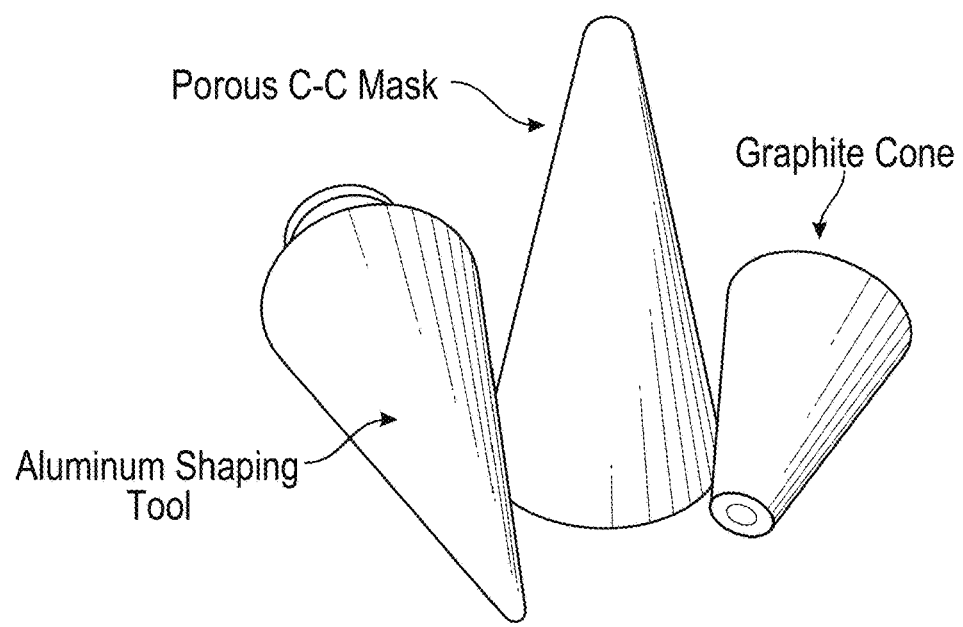
FIGS. 1A and 1B illustrate example embodiments of a cone at varying stages of the manufacturing process according to various embodiments of the present disclosure.

A method and system for determining a distance for a test probe, such as an anemometer, from a material to measure a local permeability is discussed herein. A test probe obtains measurements of a velocity with respect to gradient pressure at multiple distances from a surface of a material. According to one embodiment, the test probe is placed at a first position relative to the surface of the material. A correlation of the velocity to the gradient for the multiple distances can be determined. A test distance can be determined based on the correlations. The distance having the highest coefficient of correlation ($R^2$) can be determined as the test distance or preferred distance from the surface of the material to locate the test probe. Once the test distance is determined, test measurements can be performed by the test at multiple positions at a fixed test distance. Based on the test measurements, the local permeability of the surface of the material can be determined for the multiple positions.

The test probe can be calibrated before being used for test measurements. According to one embodiment, the test probe performs measurements while the material is omitted from a container, such as a low-speed wind-tunnel, to first determine values associated with readings from the test probe. A measurement of a fluid flow can be measured by a fluid flow measuring device. For example, the flow of a gas, such as nitrogen, can be measured by a pitot-static tube in the container. An output voltage of the test probe can also be obtained at a substantially simultaneous time. For example, a voltage output of a hot-film anemometer can be determined at a substantially same time as the pitot-static tube measurement. The output of the test probe can be calibrated based on the velocity of the fluid measured by the fluid flow measuring device compared and/or correlated to the voltage output of the test probe. The test probe can be a constant temperature anemometer, a hot-film anemometer, and/or other measuring device.

According to one embodiment, the system to measure the local permeability of the surface of the material includes a test probe positioned perpendicular to the material and a control system configured to adjust a distance from a material and to adjust the position of the test probe parallel to the material. The test probe can be configured to sense a velocity of a fluid. The control system can be configured to move the test probe to multiple distances away from a surface of the material at a first position of the surface of the material. The control system can also move the test probe to multiple positions at a distance determined to be a preferred test distance. In one embodiment, the test distance is the distance from the surface of the material at the first position that has the highest correlation coefficient of the distances.

The test probe can perform a measurement of a velocity with respect to gradient pressure at each of the distances. Based in part on the measurements, the control system can determine correlations of the velocity to the gradient for each of the distances. The test probe can also perform measurements of a velocity at the test distance for each of the positions. The control system can determine a local permeability of the material at each of the positions based in part on the measurements of the velocity at the test distance.

Reusable thermal protection systems (TPS) development can provide solutions for a variety of technical challenges, such as long-duration flights in the hypersonic regime. The aerodynamic and the material performance can be related to the near-wall effects. Indeed, the viscous dissipation within the hypersonic boundary layer can generate surface temperatures for which the strength and the environmental durability of the material is exceeded. Carbon and ceramic based materials are not able to sustain the generated surface temperatures for a prolonged exposure time. In such type of environment, active cooling systems can preserve the thermostructural integrity of the vehicle. The issuing phenomenon near the wall can generate a protective layer of coolant that can prevent active oxidation phenomena, which can quickly deteriorate carbon-carbon (C—C)/silicon-carbide materials, when particular combinations of elevated temperatures and low oxygen partial pressures occur at the surface.

The surface temperatures for C—C flat faces material and ceramic axisymmetric surfaces can be reduced by using transpiration cooling techniques. Two different gaseous coolant fluids (nitrogen and argon) and liquid water can be blown using arbitrary flow rates. When using liquid water as a coolant, ice can form, which can necessitate coupling the boundary-layer flow with the thermal response of porous materials to build up an efficient TPS based on transpiration cooling. The presence of non-uniform cooling timescales can be shown by an infrared map of conical surfaces. In one example, during the filling time of the material, the stagnation point region cools down slowly with respect to the straight sidewall of the cone because of the higher external pressure that lowered the driving force needed to push the water outside the pores.

The non-uniform distribution of the cooling power due to the pressure field of the external flow can be even accentuated if candidate TPS materials having highly anisotropic voids' structure and variable thickness are considered. Under these conditions, the characterization of the local blowing can enable avoiding hot spots on the exposed surfaces during a TPS qualification test, which can be caused by insufficient coolant flow rate. The characterization can improve the prediction capability for the thermomechanical response of TPS based on transpiration cooling.

Reusable TPS can also enable using hypersonic vehicles as practical, long-range, and affordable transportation. Extreme thermal loads generated by viscous dissipation across a hypersonic boundary layer can increase if temperature is high enough to cause the dissociation of oxygen. The thermostructural integrity of the TPS can be drastically reduced when particular combinations of elevated temperatures coupled to low partial pressures of oxygen occur and the active oxidation of the exposed surface are initiated. The transpiration cooling through a porous medium can be used because of its higher cooling effectiveness in terms of wall-temperature reduction, coolant saving, and minimum disturbance of the external flow with respect to other active cooling techniques.

The effective properties of the TPS structure can be determined with the material characterization by using non-destructive evaluation (NDE) techniques. The effective properties of the TPS structure can be drastically different at the full-scale level due to the geometry, system integration, and intrinsic defectology coming from the manufacturing process. The latter dependence can be of greater influence for materials constituted by two or more components (e.g., composite materials, alloys, etc.). X-ray computed tomography (CT) can be used to characterize the internal porous lattice of a highly porous carbon-carbon (C—C) structure. X-ray CT provides higher spatial resolution with respect to thermal tomography and lacks structure superposition and signal dispersion. The structure superposition and signal dispersion can affect conventional x-ray radiography and ultrasonic techniques.

The output data from the CT scan can facilitate defining guidelines needed to correctly perform the local effective permeability measurements. Two-dimensional (2-D) sectioning and the three-dimensional (3-D) digital reconstruction of the specimen can be used to calculate, first, the internal porosity of the prototype specimen and, then, to define the minimum dimension of the characteristic area, or control surface (CS), to be probed for the mass flux measurement. The CS can be the characteristic area that allows obtaining meaningful velocity measurements, by using a hot-film anemometer, in terms of minimum fluctuations of the mean velocity field. Additionally, the statistical analysis of both the average diameter and the spacing of the channels can be used to define the Reynolds number based on a diameter of the channels. This information can be used to determine the correct distance of a hot-film sensor from the wall. This analysis can be used to determine the probing distance for which a near-contiguous transversal wall velocity is obtained while avoiding any local effect, due to the intermittency of the material—pore interface that can alter the measurements when the distance from the wall is very small.

The permeability can be regarded as the capability of a selected material of allowing a determined fluid to pass through its internal tortuous structure. The permeability can include hydraulic conductivity and/or flow conductivity. The permeability, as well as the porosity, is a geometric property of porous media but, contrary to the porosity, the permeability can depend on the morphology of the internal network, such as pore size distribution, connectivity, porosity itself, or other factors. Composite materials having similar porosity, for example, low-porosity carbon foams and highly porous C—C layered materials, can have different permeability values due to the connectivity of the voids, such as the presence of closed pores, blind channels, and other factors, diversified tortuosity, and voids' dimensions. Because of the difficulty to model the features of lattice, there is a lack of established correlations for consolidated media. The consolidated media can include layered composite materials. The permeability parameter can be necessary to predict the pressure drop across the high- and low-pressure sides of the specimen and to guarantee the structural integrity of the porous media. The permeability distribution for transpiration cooling of reusable TPS can be necessary for selecting the correct control pressure, such as high-pressure side of the material, needed to reproduce the blowing profile/mass-flux distribution simulated numerically, which can be prescribed by the cooling requirement once the low-pressure field is imposed by the external flow. Permeability is related to the characteristic flowfield inside the porous network and different simplified relations can be used to calculate the characteristic resistance that the fluid encounters when flowing across the tortuous void structures. Darcy's law, shown in Eq. 1, is an example of a simplified relation that describes the permeability dependence, and is valid in the case of laminar, non-inertial flow, such as creeping or Stokes flow:

$$U_D = -\frac{\overline{\overline{K}}}{\mu_f} \cdot \nabla P \qquad (1)$$

The average permeability tensor ($\overline{\overline{K}}$) can be calculated once the driving force $\nabla P$, the average velocity across the probed area (Darcy's velocity $U_D$), and the fluid viscosity $\mu_f$ are known. The formal derivation of Darcy's law can be obtained from the averaging technique of the Navier-Stokes (N-S) equations applied to a reference elementary volume (REV) being statistical in terms of porosity. The averaging process on the entire domain can be necessary because N-S equations inside the fluid domain can be difficult to solve due to the complex internal geometry of porous medium and due to the difficulty of defining the boundary conditions. The averaging technique coupled to the average theorem can lead to a modified steady-state momentum equation that describes the fluid flow through the porous medium as shown below in Eq. 2. Eq. 2 can be simplified in base of the flow regime inside the porous lattice:

$$\rho_f \langle \langle u \rangle \cdot \nabla \rangle \langle u \rangle = -\nabla \langle P \rangle + \mu_f \nabla^2 \langle u \rangle - \frac{\mu_f}{\overline{\overline{K}}} \varepsilon_{3-D} \langle u \rangle \qquad (2)$$

where $$\langle u \rangle = \frac{U_D}{\varepsilon_{sup}} \qquad (3)$$

The angled brackets in Eqs. 2 and 3 indicate the averaged quantities across the REV and $\varepsilon_{sup}$ is the porosity of the external surface where the velocity measurements are performed (superficial porosity). The discriminant parameter used to define the flow regime is the Reynolds number based on a characteristic dimension of the voids. The characteristic length scale used to define the Reynolds number for consolidated porous media can depend on the conformation of the internal network. The average diameter of pores can be selected as the characteristic dimension for metallic and composite foams. The average diameter of the fibers, or the hydraulic diameter based on the radius and the volume fraction of the fibers, can be used for fibrous composite materials.

According to one example, the average diameter for channels is used to define the Reynolds number because it is a small characteristic dimension and has the higher impact on defining the pressure drop across the thickness of the material of a layered C—C material. Both the inertial term, as shown on the left-hand side of Eq. 2, and the viscous term, as shown in the second term on the right-hand side in Eq. 2, can be neglected when the flow is laminar, such as when $Re_{ch} \leq 10$. According to this embodiment, the averaged momentum equation is reduced to the generalized Darcy's law as shown in Eq. 1 and the variation of the pressure gradient with respect to the variation of Darcy's velocity is linear, for example, having a constant permeability.

In another example, when $Re_{ch} > 10$ and $Re_{ch} \leq 300$, the inertial term (Forchheimer correction factor), the viscous term (Brinkman correction factor), and the Darcy term are the same order of magnitude, and the complete averaged momentum equation Eq. 2 can be analyzed to capture the deviation from the aforementioned linear behavior, for example, variable permeability. In yet another example, when $Re_{ch} > 300$, the flow is in the inertial range and only the Forchheimer and Brinkman correction factors can be considered to predict the pressure drop across a porous medium.

The use of Darcy's law can be verified for all the flow rates used due to the small characteristic diameter of the channels ($D_{ch} \approx 30$ μm). The flow rates can be calculated by using one or more computed tomography (CT) scan images coupled to the use of gaseous coolant fluids that lead to small Reynolds numbers. The average permeability of a porous material with respect to a selected fluid in the laminar regime can be calculated from the slope of the straight line connecting the pressure gradient to the coolant mass flux (gaseous coolant) or to Darcy's velocity (liquid coolant). The local permeability for the r direction (across-the-thickness direction) can be calculated by projecting Eq. 1 in the same direction and by integrating it across the thickness H of a material:

$$-\int_{P_{ext}}^{P_H} dP = \int_0^{-H} \frac{\mu_f}{K_r} U_D^r dr \qquad (4)$$

Eq. 4 assumes the empirical form of Darcy's law, once the average velocity and the dynamic viscosity of the fluid are assumed constant across the local thickness of the material:

$$\frac{P_0 - P_H}{H} = \frac{\mu_f}{K^r} U_D^r \qquad (5)$$

Eq. 5 is valid when determining the permeability of a material with respect to a liquid fluid. According to an embodiment in which gaseous fluids are flowing through a tortuous maze, a different expression of the left-hand side in Eq. 5 can be used. The compressibility of the gas inside the porous material can be taken into account by introducing the mean pressure in the core during the measurements, as shown in Eq. 6. The permeability with respect to gaseous fluids, as provided by Eq. 6, can approach the absolute liquid permeability, as calculated by Eq. 5, for increasing values of the mean pressure in the sample:

$$\frac{\Delta P}{H} \cdot \frac{\tilde{P}}{P_{ext}} = \frac{\mu_f}{K^r} U_D^r \qquad (6)$$

where $\tilde{P}$ is the average pressure between the high and low pressure sides of the thickness for a material. Eq. 6 is valid when the mass flux in the r direction $\rho U_D^r$ is conserved across the thickness of the material, for example when porous samples are bounded by solid walls. The standard methodology can be used to calculate the average permeability of materials having standard dimensions, such as a standard frontal area and thickness, for which the fluid is confined to flow in the direction of the thickness of the material. The average mass flux in the r direction can be considered $\overline{\rho_D U_D^r}$ in Eq. 7 when the local permeability of full scale porous structures, for which the fluid is not necessarily confined to flow in the r direction, has to be calculated:

$$\frac{\Delta P}{H} \cdot \frac{\overline{P}}{P_{ext}} \cdot \rho_{ext} = \frac{\mu_f}{K^r} \cdot \overline{\rho_D U_D^r} \qquad (7)$$

The fluid can follow different flow paths in relation to the three-dimensional network. Depending on the distribution of the actual boundaries of the structure, differences can exist between the permeability of the standard sample with respect to that of the full-scale components. The local blowing at the low-pressure side can be measured with a technique that employs hot-film anemometry while the correspondent mass flux at the high pressure side is unknown. According to one embodiment, an effective permeability $K_{eff}$ can be used to in place of the local permeability as defined in Eq. 7, when the local permeability cannot be directly calculated.

The effective permeability can be a local blowing capability of a porous material, with respect to a selected fluid, when a global pressure gradient is imposed between the thickness of the material. The effective permeability can indicate the pressure drop required to blow a prescribed coolant flow rate across a porous lattice so that the average coolant mass flux in Eq. 7 is substituted with the measured mass flux at the low-pressure side of the material. The mass flux measured on the low pressure side can be proportional to Darcy's velocity in the radial direction because, for the prescribed distance from the wall where the hot-film measurements have been performed, the coolant density can be considered constant and, therefore, Eq. 7 becomes equivalent to Eq. 6.

The presence of intrinsic defects, for example those due to the manufacturing processes, can induce asymmetric flow paths and non-uniform heat-transfer coupling between the coolant fluid and the porous matrix. As a result, concentrated mechanical loads and hot spots on the exposed surfaces can generate, which can modify the nominal thermomechanical response of the entire TPS.

Figure 1B:
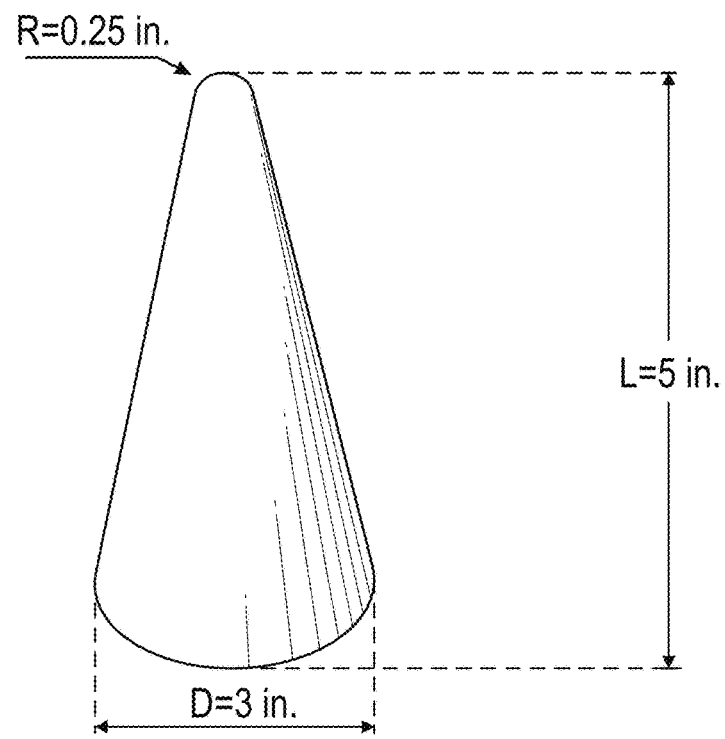

With reference to FIGS. 1A and 1B, shown is an example embodiment of a material. FIG. 1A shows the C—C material during the manufacturing process after a layup stage. FIG. 1B shows the C—C material in the final stage of the manufacturing process after pyrolysis and surface finishing. The C—C material is shown as porous C—C mask with a graphite cone and an aluminum shaping tool. The C—C material is an example embodiment of a complex porous structure for which the use of the permeability measurements obtained by standard methodology would be imprecise due to the structural morphology and unavoidable defectologies. The axisymmetric composite mask shown in FIG. 1B is characterized by having variable thickness, high porosity prescribed at the manufacturing stage, diversified surface finishing in comparison from FIGS. 1A and 1B, and boundary constraints on the structure. This generates highly asymmetric flow paths inside the tortuous structure.

With reference to FIG. 2, shown is an assembly of the C—C nose according to various embodiments of the present disclosure. The structure can be composed of a truncated graphite cone that has the purpose of providing the coolant up to the internal plenum and mechanically supports the hollow transpiring C—C cone. The external sliding mask along with an internal O-ring can be used to seal between the C—C mask and the graphite support. The variable thickness region can be sized to support a variable transpiration capability throughout it.

Figure 3:
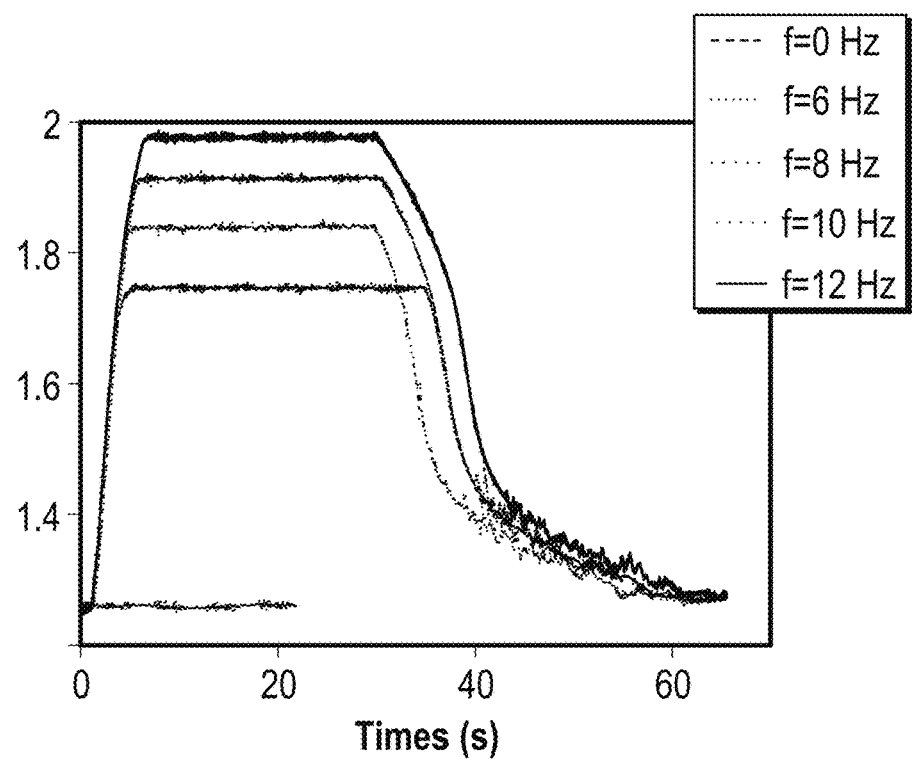
FIG. 3 is a graph representing outputs for different wind frequencies according to various embodiments of the present disclosure.

A hot-film anemometer can be used to conduct mass-flux measurements on the outer surface of the material. The measurement system can be composed of a hot film used in conjunction with a constant temperature anemometer (CTA). In one embodiment, the hot file is a TSI-1210-20 with a 50.8 μm diameter and the CTA is a TSI-1750. In this embodiment, the control resistance of the CTA is selected to impose an over-heat ratio of the hot film equal to 1.35, which corresponds to a film temperature of about 441 K. The high nominal value of the film temperature with respect to the ambient temperature can ensure a high sensitivity of the sensing film to the variations of the blowing velocity. The calibration of the hot-film sensor can be performed in a low-speed wind-tunnel. Simultaneous calibrated pitot-static pressure measurements of the freestream velocity can be acquired in the low-speed wind-tunnel. The calibration process can correlate the output voltage of the hot film (FIG. 3) with the velocity measurements from the pitot-static tube. The mass flux measured by the hot-film sensor can then be related to the velocity calculated from the pitot measurements.

Temperature corrections, as shown in Eq. 8, for the measurements during permeability tests can be considered to compensate for the difference in temperature that naturally occurs between the calibration process and the permeability tests:

$$V_{cal} = \sqrt{\frac{(T_{HF} - T_{cal})}{(T_{HF} - T_m)}} \cdot V_m \qquad (8)$$

Figure 4:
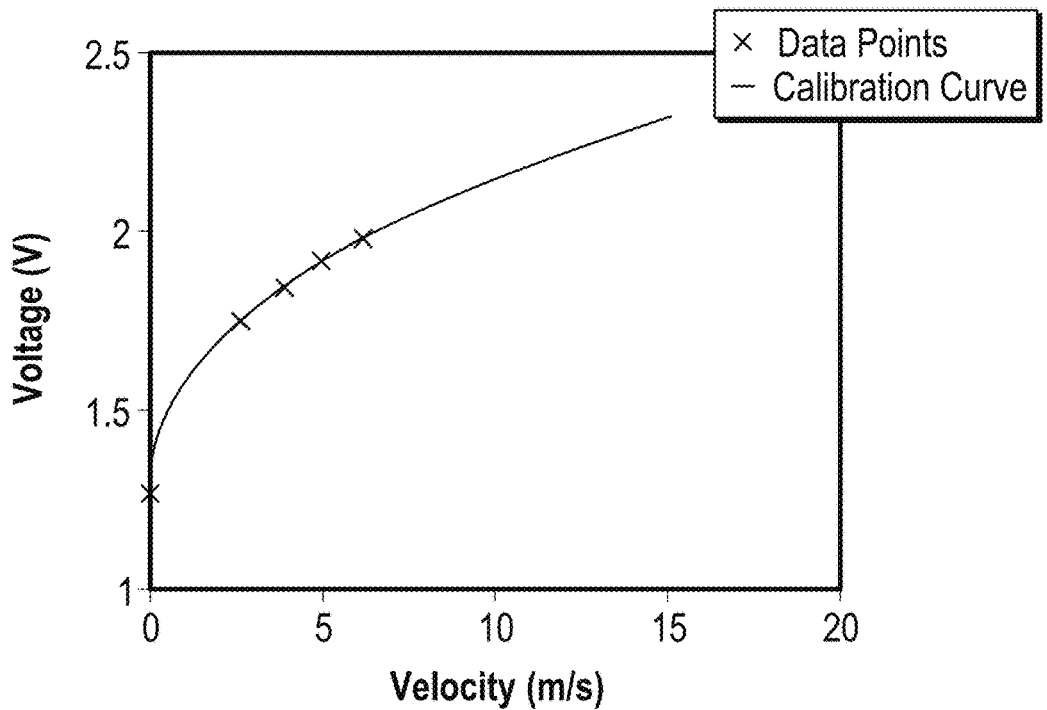
FIG. 4 is a graph representing a calibration curve according to various embodiments of the present disclosure.

The energy equation written for a control volume coincident with the film can lead to an expression of the Nusselt number when the film temperature is kept constant by the CTA. The Nusselt number can be correlated to the Reynolds number based on the diameter of the film. The use of a power-law correlation can be used for the range of Reynolds number expected because the power-law correlation provides the lower root-mean-square error as shown in FIG. 4. The uncertainty on the calibration curve can be calculated from the errors pertaining to both the hot-film corrected output voltage $V_{cal}$ and the velocity calculation from the pitot-static tube measurements. The uncertainties on the voltage can be calculated from the standard deviation of the hot-film output signal, whereas the uncertainties on the flow velocities can be estimated based on the propagation of the errors on the Bernoulli equation given the accuracy of the static and total pressure sensors.

Figure 2A:
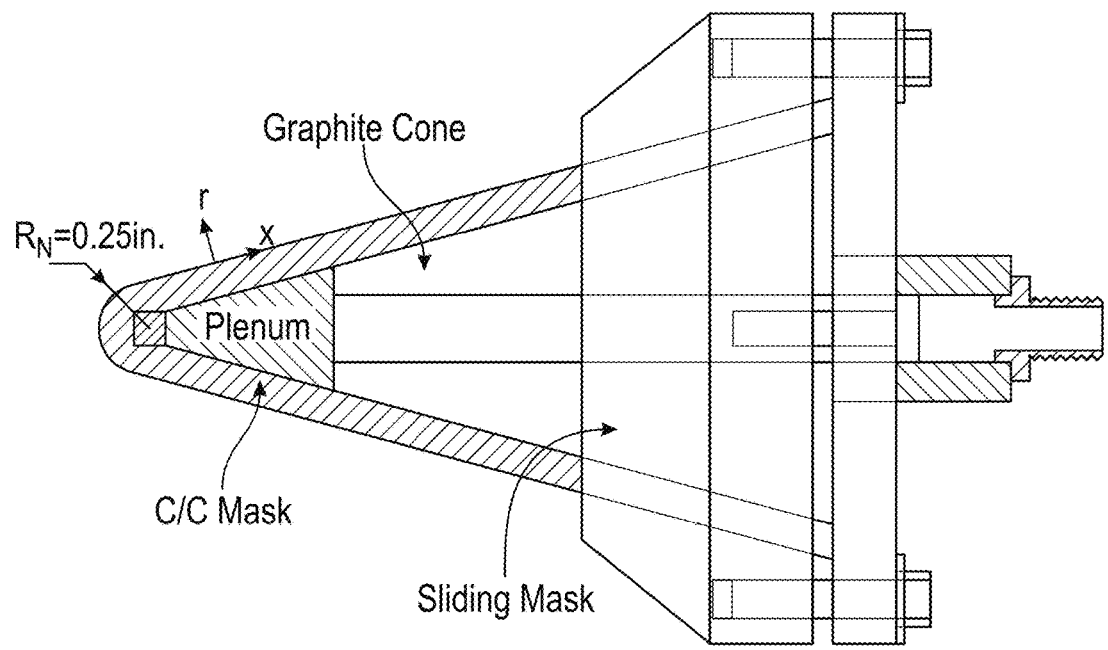
FIGS. 2A and 2B illustrate examples of a CAD model and a material according to various embodiments of the present disclosure.
Figure 5A:
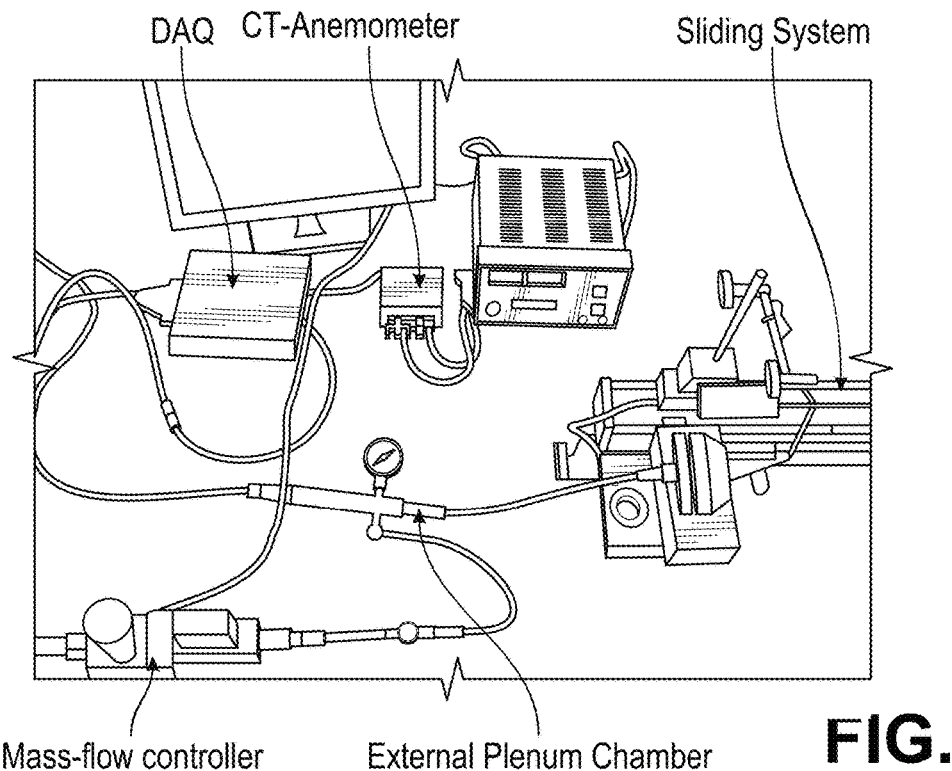
FIGS. 5A and 5B illustrate a setup for permeability measurements according to various embodiments of the present disclosure.
Figure 5B:
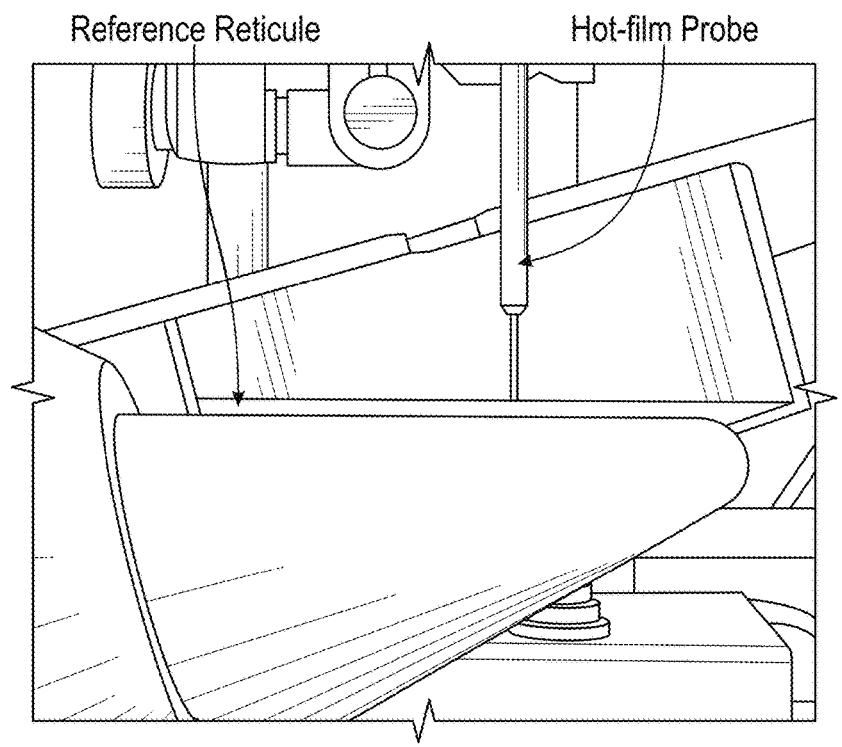

Characterizing the full-scale material, in terms of the local effective permeability, can leverage the capability of being able to measure the local mass flux blown from a porous wall at ambient pressure once the stagnation conditions are obtained on the other side of the material, for example, as shown in the internal plenum chamber in FIG. 2A. A precise traversing system can be used to move the hot-film parallel to the surface of the material as illustrated in FIG. 5A. In FIG. 5B, shown is a calibration reticule and an optical alignment system that can be used to provide a perpendicular position between the hot film and the porous wall of a material. The calibration reticule and the optical alignment system provide for a minimization of the angularity effects that impact the hot-film measurements. In one example, the total pressure in the plenum of a sample $P_{st}$ is measured inside the external plenum chamber of FIG. 5A, which is located between the C—C nose tip and the mass-flow controller. The dimension of the external plenum provide for the same pressure conditions inside the internal chamber between the C—C mask and the graphite support (FIG. 2A). In one embodiment, the pressure losses inside the pipe that connect the external to the internal plenum are negligible. The output signals from the pressure transducer and from the CTA system can be acquired by using a 16-bit data acquisition system, shown as DAQ in FIG. 5A.

Figure 6A:
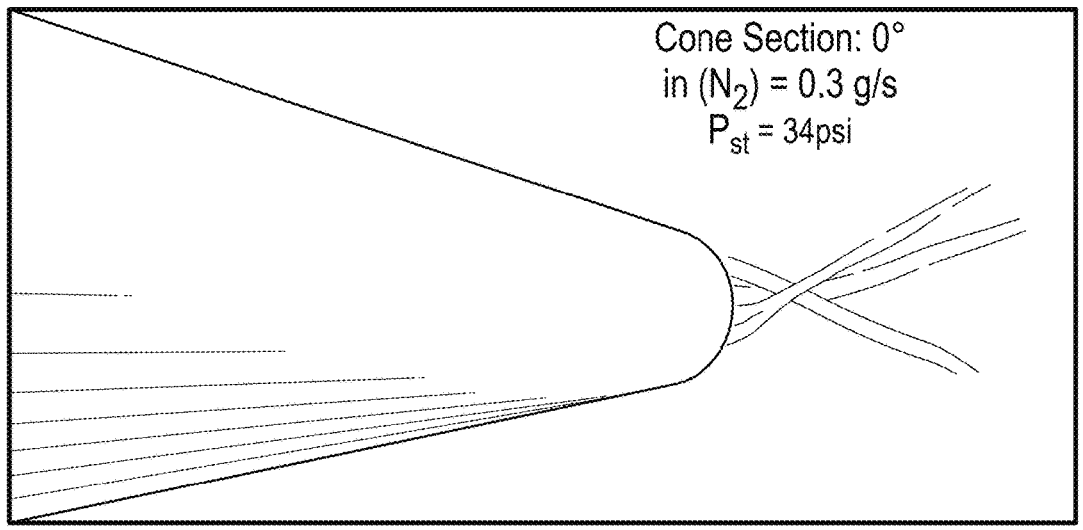
FIGS. 6A and 6B illustrate an example of Schlieren photographs according to various embodiments of the present disclosure.
Figure 6B:
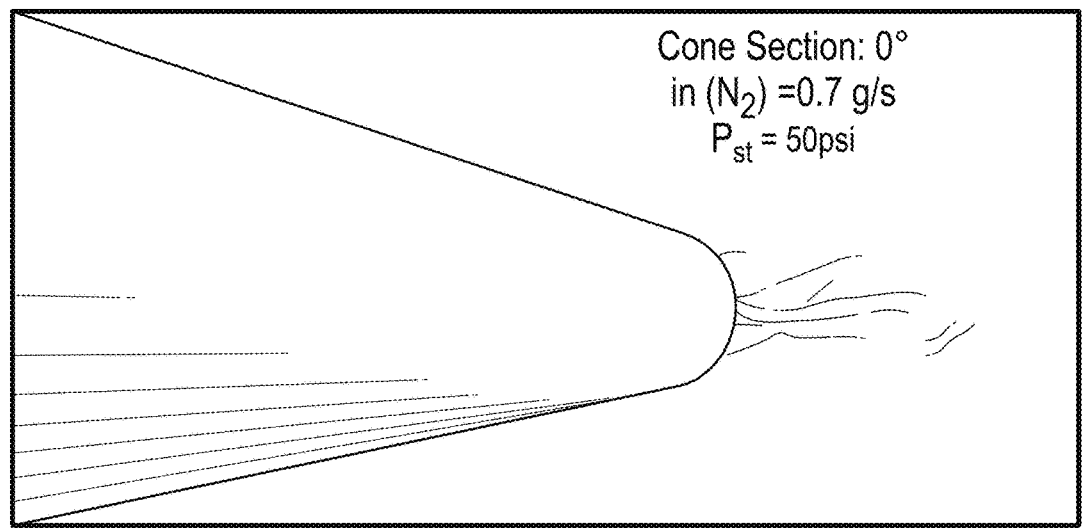

The mass flux measured by maintaining the hot wire at an appropriate distance from the surface can be related to the blowing velocity by means of the calibration curve in FIG. 4 once the density change at the measurement points is negligible. A Schlieren test can verify this relation using a gas, for example nitrogen, with the scope of detecting any sharp changes of density at the exit of the pores. No remarkable variations of the density on the straight sidewalls of a material, such as the material shown in FIG. 6, have been determined. A significant change of the refraction index of the coolant fluid blown from the pores can be detected near the stagnation point (SP) region of the nose tip, which is due to the presence of two radial delaminations that span through the entire nose-tip length.

Figure 7A:
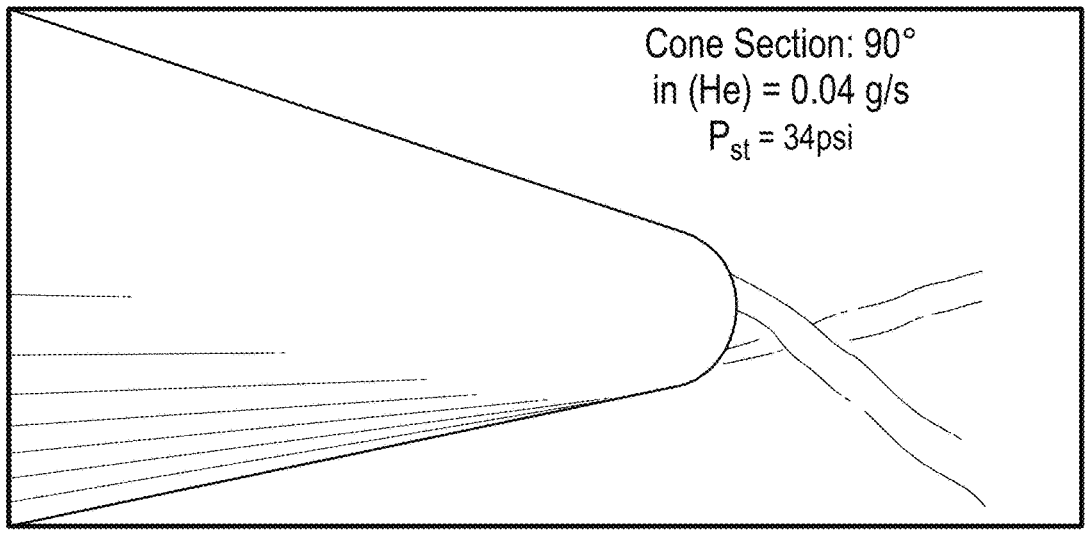
FIGS. 7A and 7B illustrate an example of Schlieren photographs according to various embodiments of the present disclosure.
Figure 7B:
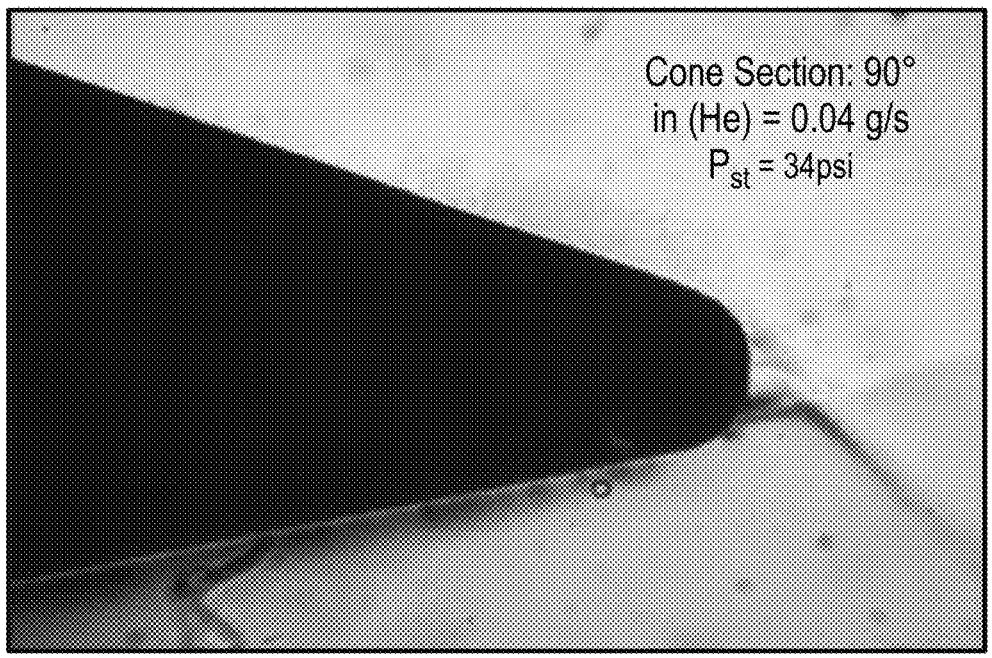

One or more Schlieren tests, using helium as working fluid, can be performed using a gas, for example helium, as a working fluid for different longitudinal planes with the purpose of detecting, qualitatively, the transpiring capability along the sidewall of the material in FIG. 7. An example color map for the Schlieren images is shown in FIG. 7B to emphasize the blowing profile. FIGS. 7A and 7B show the injection points near the stagnation region, the blowing on the straight walls of the material, and a near-zero transpiration in the corner region of the nose tip. The Schlieren tests on different sections of the cone can reveal different blowing profiles. The different blowing profiles can highlight the presence of an asymmetric blowing capability due to the anisotropy of the internal void structures. Examples of nominal conditions selected for transpiration measurements are reported in Table 1.

TABLE 1

Nominal test conditions used for the permeability tests

| Test no. | $\dot{m}_{air}$, SLPM | $\dot{m}_{air}$, g/s | $\overline{P_{sp}}$, Psi |
|---|---|---|---|
| 1 | 12 ± 3 | 0.259 ± 0.067 | 34.80 ± 0.38 |
| 2 | 14 ± 3 | 0.302 ± 0.067 | 38.02 ± 0.33 |
| 3 | 16 ± 3 | 0.345 ± 0.067 | 39.83 ± 0.61 |
| 4 | 18 ± 3 | 0.388 ± 0.068 | 45.35 ± 0.06 |
| 5 | 20 ± 3 | 0.431 ± 0.068 | 48.71 ± 0.55 |

The minimum value of the mass-flow rate can be chosen to minimize the influence of the noise from the background velocity in the surrounding area room to maximize the signal-to-noise ratio. The upper bound value can be imposed by generating a high differential pressure to guarantee the structural integrity of the material. The nominal test conditions of Table 1 were targeted for three of the four longitudinal cut planes shown in FIG. 8A. Eleven locations for each plane can be surveyed with the hot-film probe as illustrated in FIG. 8B.

Figure 8A:
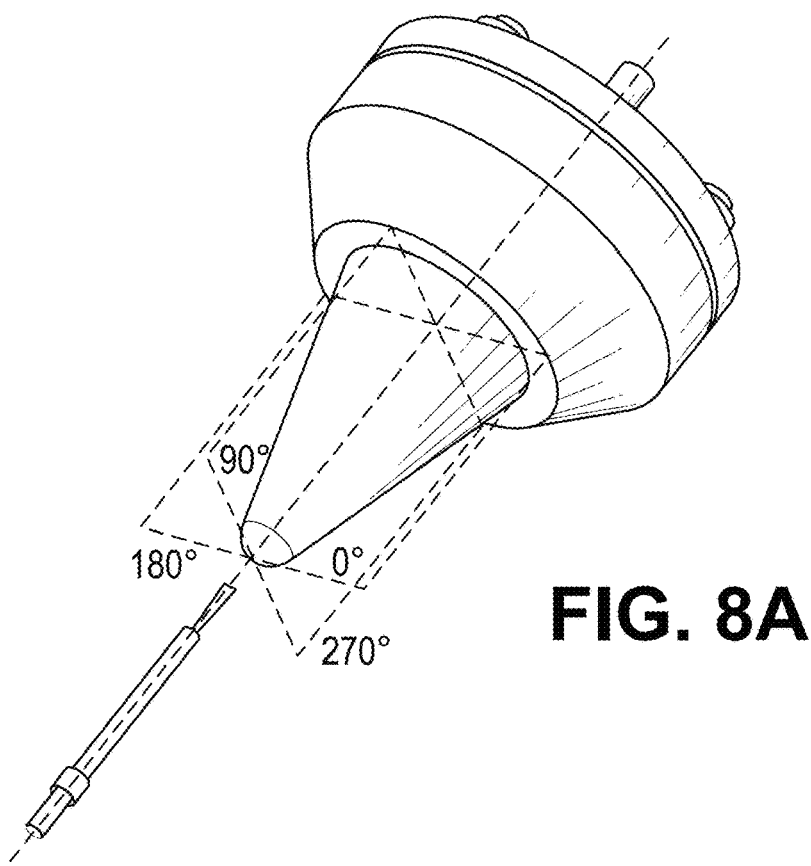
FIGS. 8A and 8B illustrate an example of probe placement and a material according to various embodiments of the present disclosure.
Figure 8B:
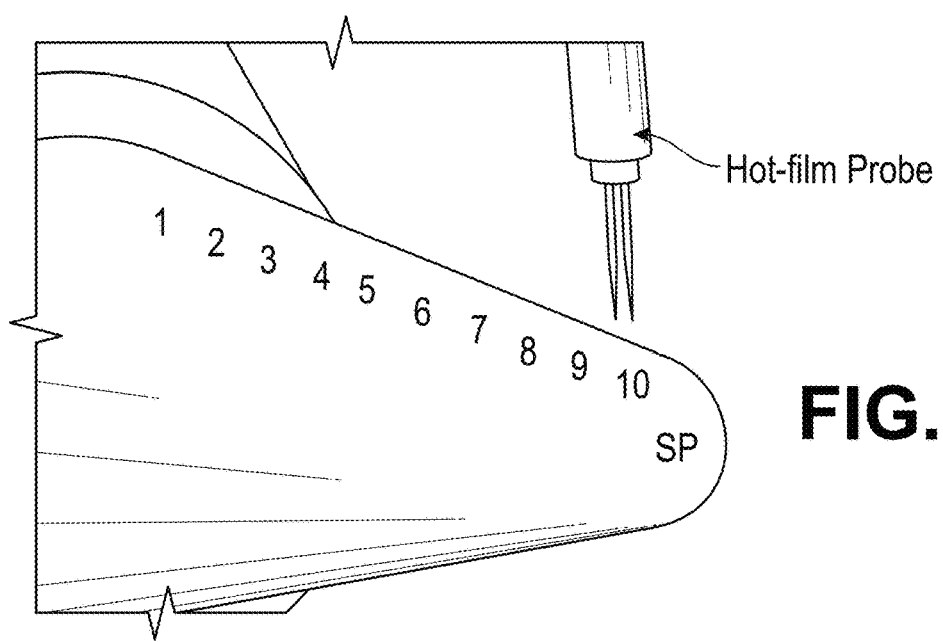

The longitudinal spacing of the control points (CPs) can be determined to provide a good spatial resolution for the calculation of the effective permeability as shown in FIG. 8B. In an example embodiment, the longitudinal spacing of the CP can also be determined to by scanning the transpiring properties of the mask for the following regions: 1) the stagnation point region, 2) the straight sidewall above the graphite support (CP1-CP3), 3) the straight sidewall above the plenum region (CP4-CP9), and 4) the corner region (CP10). More than one orientation of the sensing file can be used to prove the stagnation point region. According to one embodiment, two orientations of the sensing film can be used to probe the entire stagnation point region. SP horizontal and SP vertical represent the position of the hot film perpendicular to the 90-270 degree plane in FIGS. 8A and 9A and perpendicular to the 0-180 degree plane in FIG. 9B, respectively.

The distinction between the longitudinal and transversal orientation of the hot-film probe provides ensures the two radial delaminations that created a strong asymmetric velocity field in correspondence to the SP region. The remaining 10 points along the surface of the material can be determined with only the orientation perpendicular to the axis of the cone, shown in FIGS. 5B and 8B because, contrary to the SP region, the significant difference determined by a survey near the overall diameter of the control surfaces (CSs) is negligible in terms of average velocity. According to one embodiment, the velocity measurements are collected at the center of the CS, and all results are referred to the CPs. The round control surfaces have a diameter $D_{cs}$=0.1 in. The dimension of the control surfaces can be based upon the minimum size of the representative area that permits considering the blowing statistically constant across the surveyed control points. The characteristic diameter of the control surfaces, which can also determine the spatial resolution of the permeability map, can be defined by a convergence criterion based on the average-porosity calculation.

Figure 10:
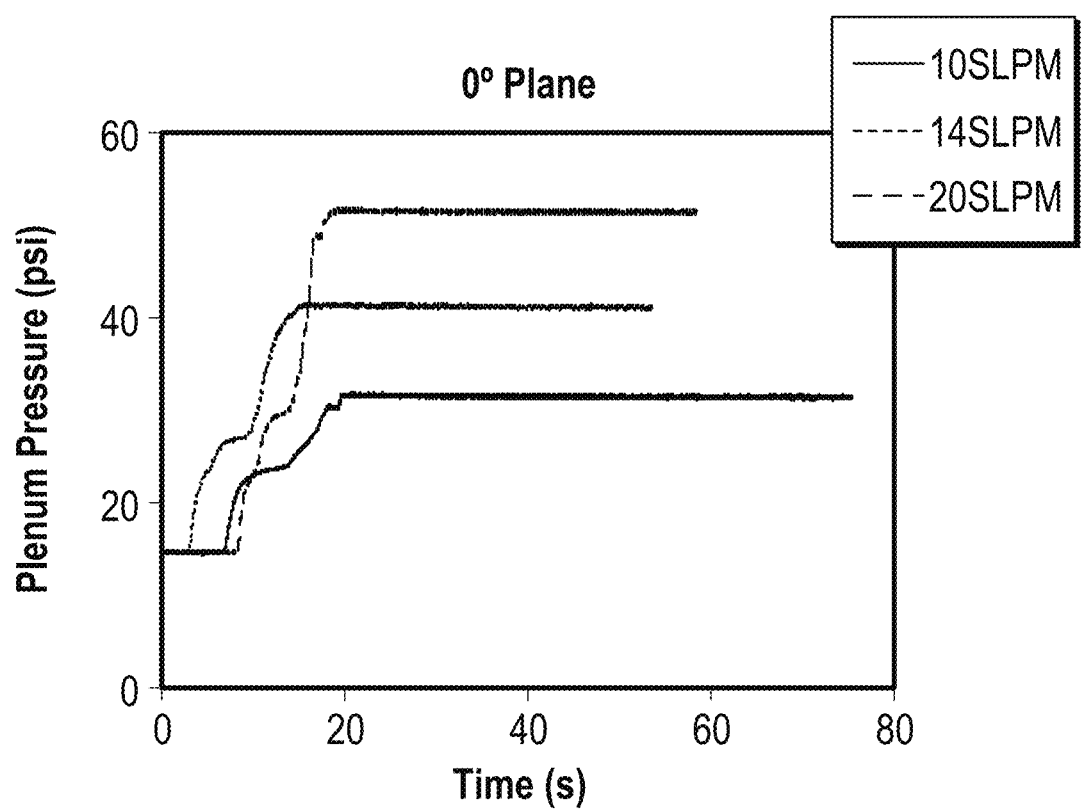
FIG. 10 is a graph representing an example of external-plenum pressure at airflow rates according to various embodiments of the present disclosure.

The mass-flux measurements can be recorded once the plenum pressure reached the steady state as illustrated in the chart of FIG. 10. The mass-flux measurements can also be recorded once a hot-film probe has been placed at the center of each control surface for the time needed to obtain a meaningful measurement in terms of uniform fluctuations of the mean output voltage, for example, greater than 5 seconds.

The influence of the probe distance from the wall can be determined by applying the theory of fluid flow through perforated plates/screens that allowed identification of the range of optimal distances for the mass-flux measurements. A proper probing position is necessary to obtain meaningful velocity measurements in terms of minimum fluctuations with respect to the mean velocity field. In the near-wall region, single jets can be discernable with a pattern that mimics the "perforated" arrangement of the porous surface, whereas at the merging distance $L_m$, the jets coalesce together.

The hot-film can cross low and high velocity regions with the periodicity of the pores pattern when the hot-film is moved parallel to the surface at a distance $r<L_m$. The velocity fluctuations increase continuously at the merging distance ($r=L_m$). When r is slightly higher than the merging distance, a near-continuous blowing velocity can be detected. The merging length can depend on the network mesh size M and on the Reynolds number based on the diameter of the channels $Re_{ch}$. In one embodiment, below a certain critical Reynolds number ($Re_{cr} \approx 20$), the spreading angle of the jets decreases with the Reynolds number and the merging distance follows the relation $L_m \sim M*Re_{ch}$. In this embodiment, when $Re_{ch}>Re_{cr}$ meaning the jets are turbulent jets, the spreading angle of the jets increases with $Re_{ch}$ and the dependence of the merging distance changes with respect to the Reynolds number ($Lm \sim M*Re_{ch}^{-1}$).

Figure 11A:
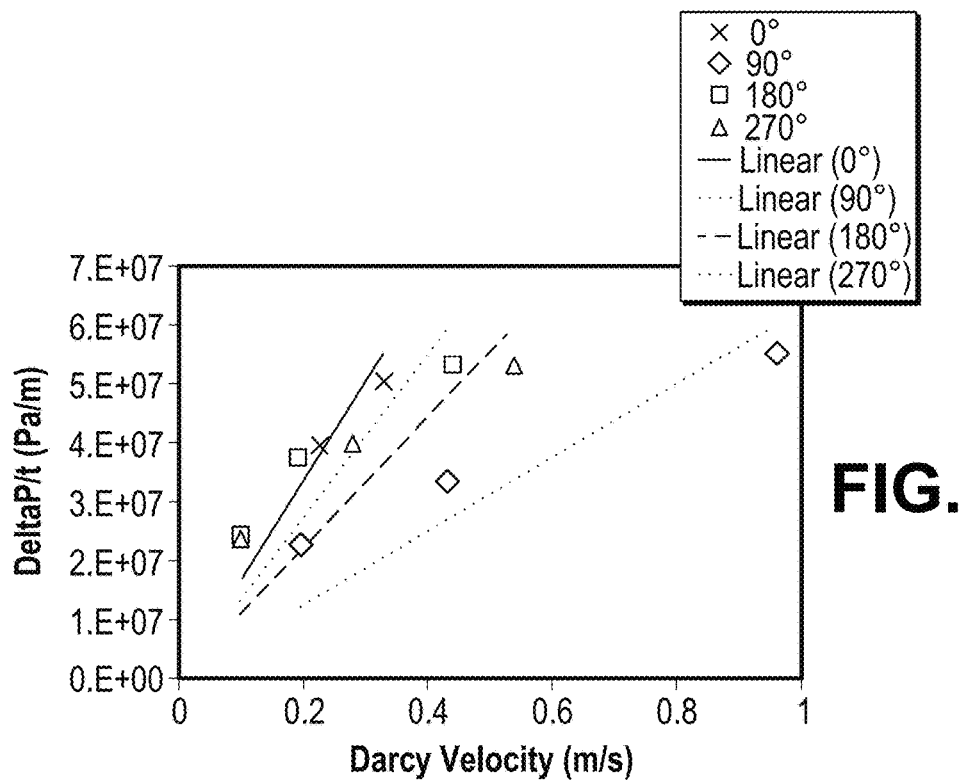
FIGS. 11A and 11B illustrate examples of data at a control point according to various embodiments of the present disclosure.
Figure 11B:
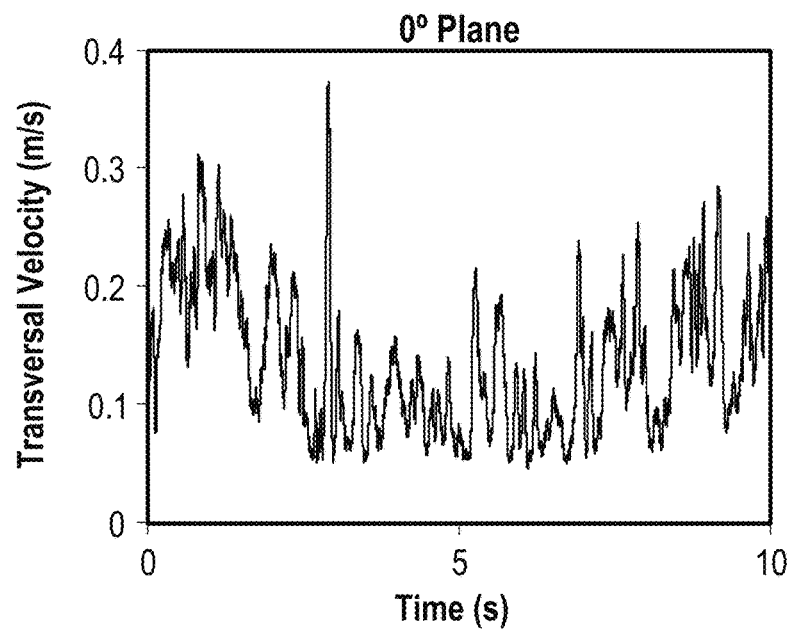

The impact of the space between the hot film and the wall on the velocity measurements can be demonstrated by performing measurements. In one example, the measurements are performed using nitrogen as the coolant fluid and keeping the hot film at $d_w=0.05$ in. from the wall. This example provided, for most of the points and planes surveyed, the scattered data of FIG. 11A, which does not correlate among each other using a linear curve fit (Darcy's law). This can be caused by the high-velocity fluctuations coming from the traces of the hot-film measurements in FIG. 11B, which are comparable to the nominal value of the mean-velocity field. The lack of correlation can be recreated when velocity measurements are performed within an interaction region of two or more co-flowing jets.

A statistical analysis of the dimensions and distribution of the void structures inside the porous network can be used to define the probing distance for which a near-contiguous transversal wall velocity can be obtained while avoiding any local effect due to the intermittency of the material/pore interface. According to one embodiment, the analysis is performed by using the output data from an x-ray CT scan of a material to be measured. In one example, the Reynolds number can be estimated based on the diameter of the channel because of the combined use of the average diameter of the throats $D_{ch}=(29.47\pm5.57)$ μm and porosity of the external surface $\varepsilon_{sup}=(0.5\pm0.1)\%$. The minimum and maximum merging distances of the single jets from the porous wall, as shown in Eqs. 9 and 10 can be calculated because of the range of variation of the characteristic network mesh size ($0.012<M<0.014$ in.) and the Reynolds number based on the average diameter of the channel ($4<Re_{ch}<13$):

$$(L_m)_{min} \sim (M)_{min} \cdot (Re_{ch})_{min} \sim 0.048 \text{ in.} \quad (9)$$

$$(L_m)_{max} \sim (M)_{max} \cdot (Re_{ch})_{max} \sim 0.140 \text{ in.} \quad (10)$$

The velocity utilized for the Reynolds number calculation, $U_{ch}$, can be the average-pore exit velocity pertaining to the specific control surface. The selection of the flow measurement device can be based on the ability to obtain the aforementioned meaningful average-pore velocity.

Figure 12A:
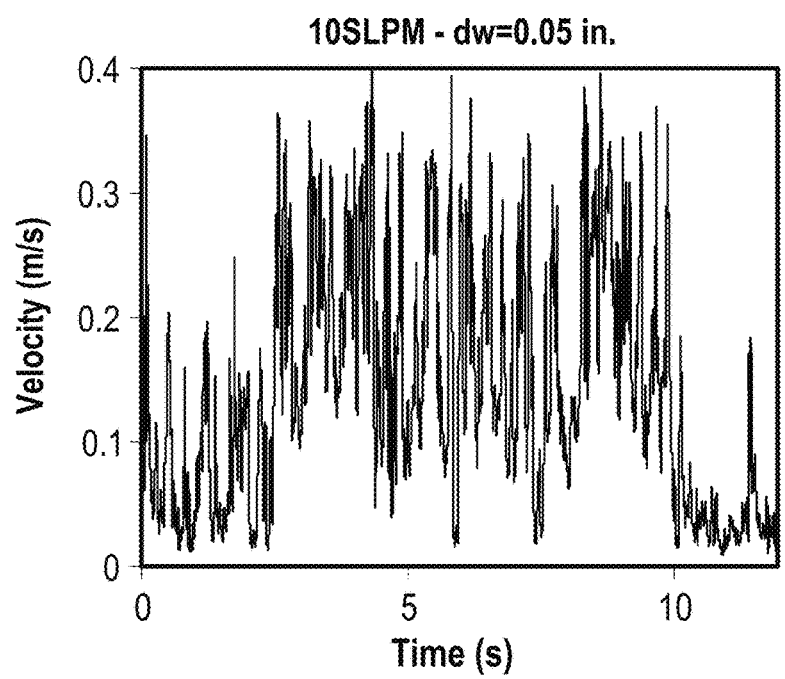
FIGS. 12A-C are graphs illustrating velocity measurements at various wall distances according to various embodiments of the present disclosure.
Figure 12B:
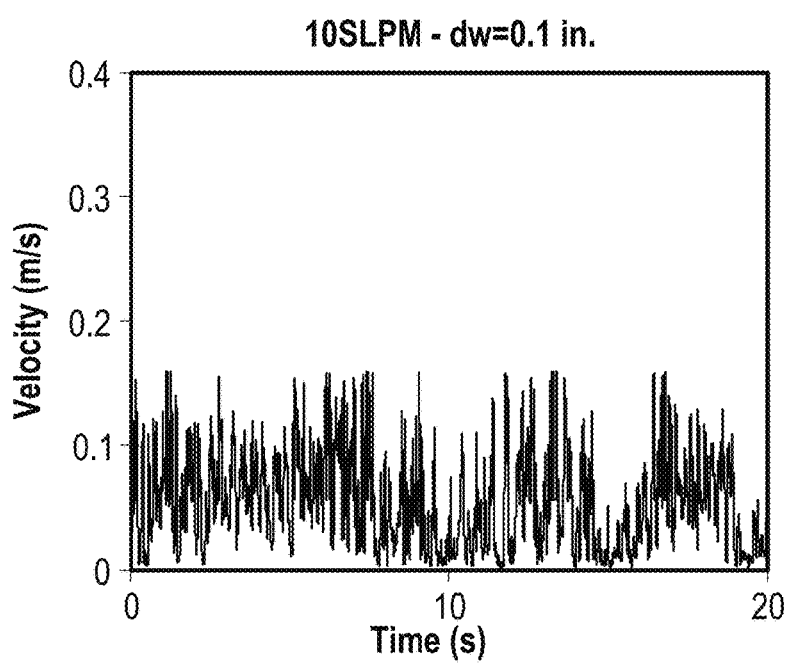
Figure 12C:
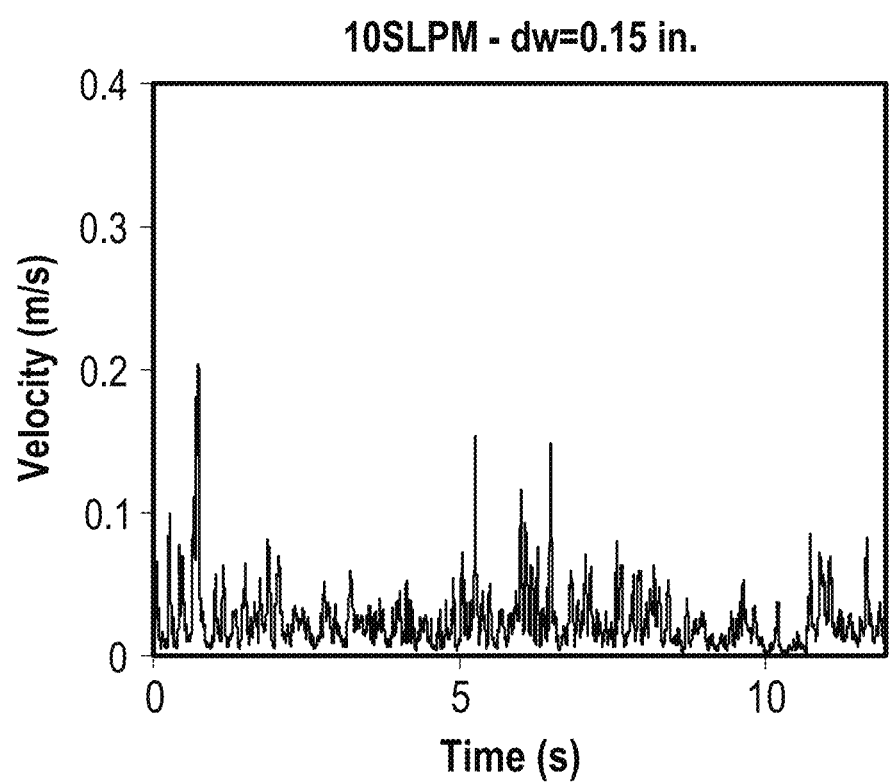
Figure 13A:
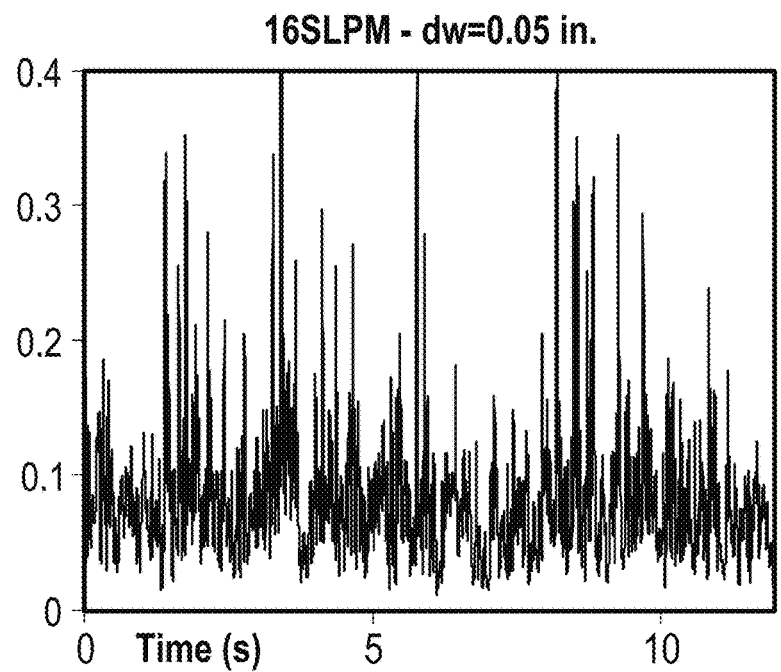
FIGS. 13A-C are graphs illustrating velocity measurements at various wall distances according to various embodiments of the present disclosure.
Figure 13B:
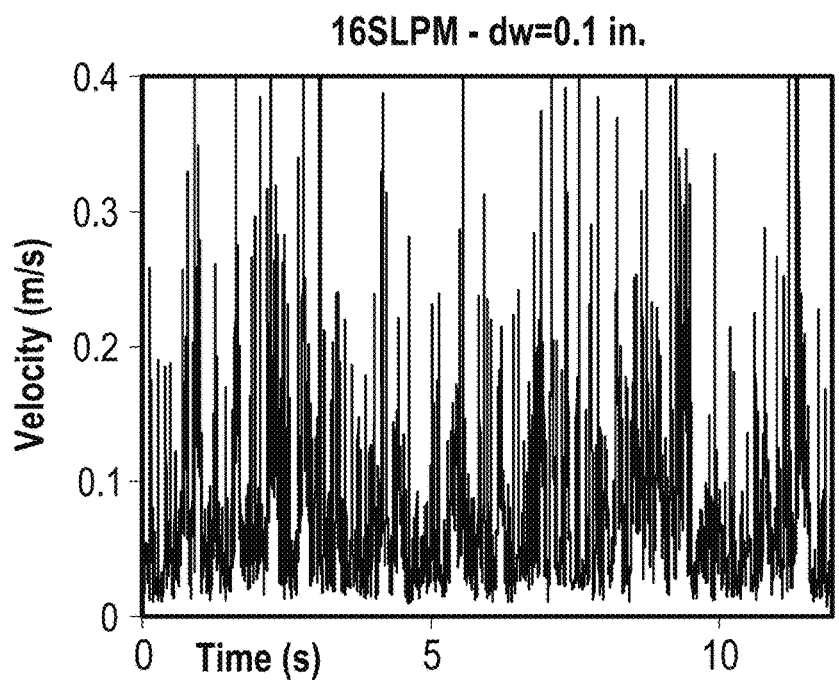
Figure 13C:
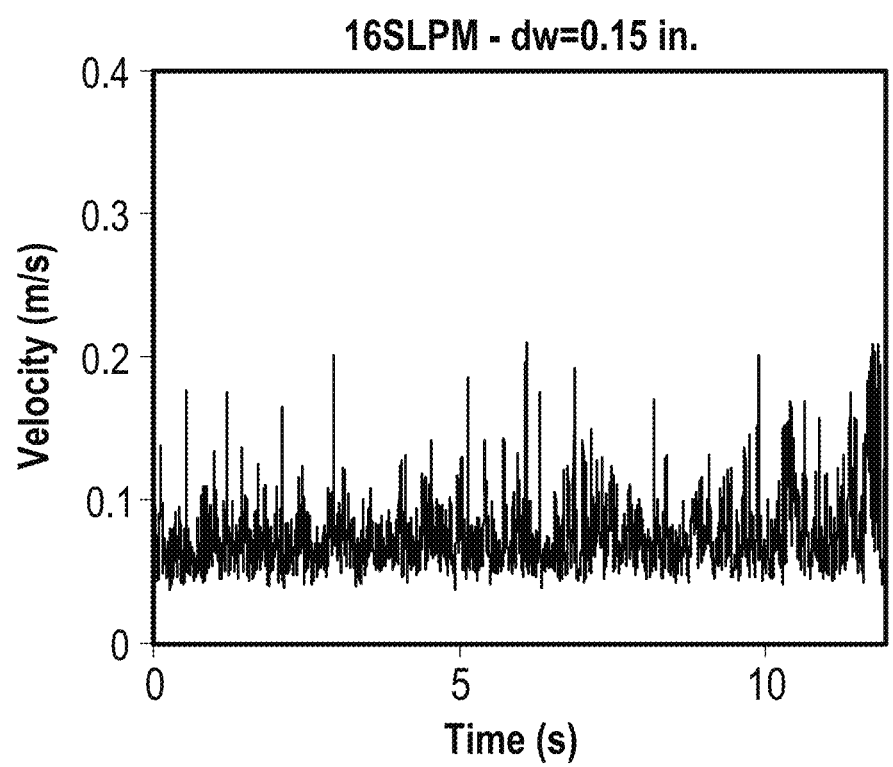

In other embodiments, additional blowing tests, using air as working fluid, can be performed at prescribed distances from the wall to verify the overall prediction on the average coalescence distance of the jets, as illustrated in FIGS. 12 and 13. In one embodiment, the coalescence distance, as determined by Eqs. 9 and 10, increased with the imposed airflow rate. For embodiment producing the measures of FIGS. 12A and 13A, the closest distance of the probe from the wall for the range of flow rates considered, produced standard deviations on the transversal wall velocity values larger than the nominal value of the mean velocity ($\sigma_U > U_D$). In this embodiment, the determined optimal probing distance for $10<m_{air}<14$ SLPM is approximately $d_w=0.1$ in for FIG. 12B because the standard deviation on the velocity measurement is lower than 50% with respect to the mean velocity.

The farther distance from the wall for the embodiment measured in FIG. 12C is not suitable for the permeability tests because of the natural velocity decay substantially downstream of the coalescence distance of the jets. The optimal probing distance for the remaining flow rates used ($m_{air}=16\div20$ SLPM) is around $d_w=0.15$ in for the embodiment measured for FIG. 13C. The highest velocity fluctuations detectable in FIG. 13b can be determined by the capturing of the merging location of co-flowing jets where local instability of the flow is generated. The results of the example embodiments in FIGS. 12A-C and 13A-C corroborate the results calculated in Eqs. 9 and 10.

Figure 14A:
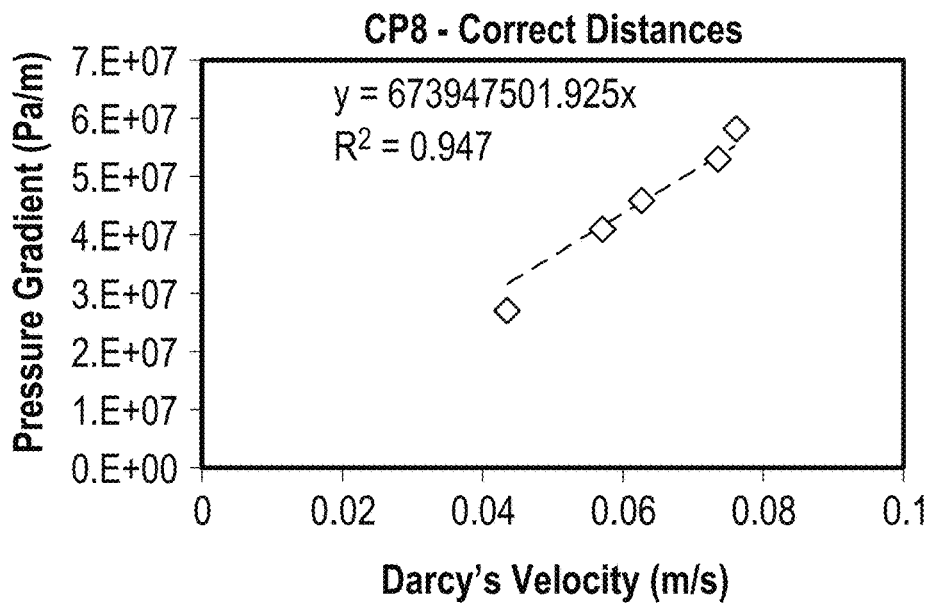
FIGS. 14A-C are graphs illustrating the curve fit of Darcy's velocity at varying distances according to various embodiments of the present disclosure.
Figure 14B:
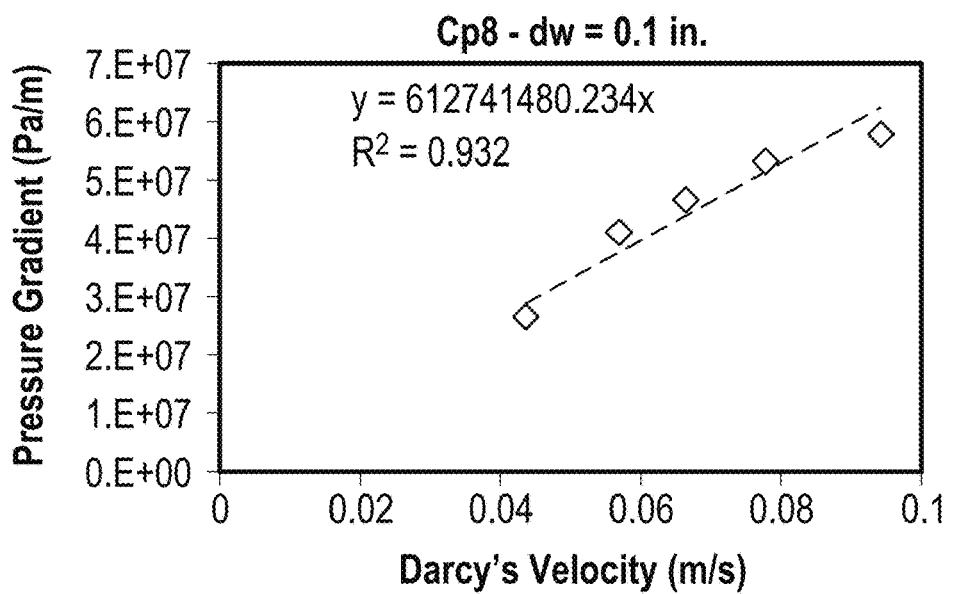
Figure 14C:
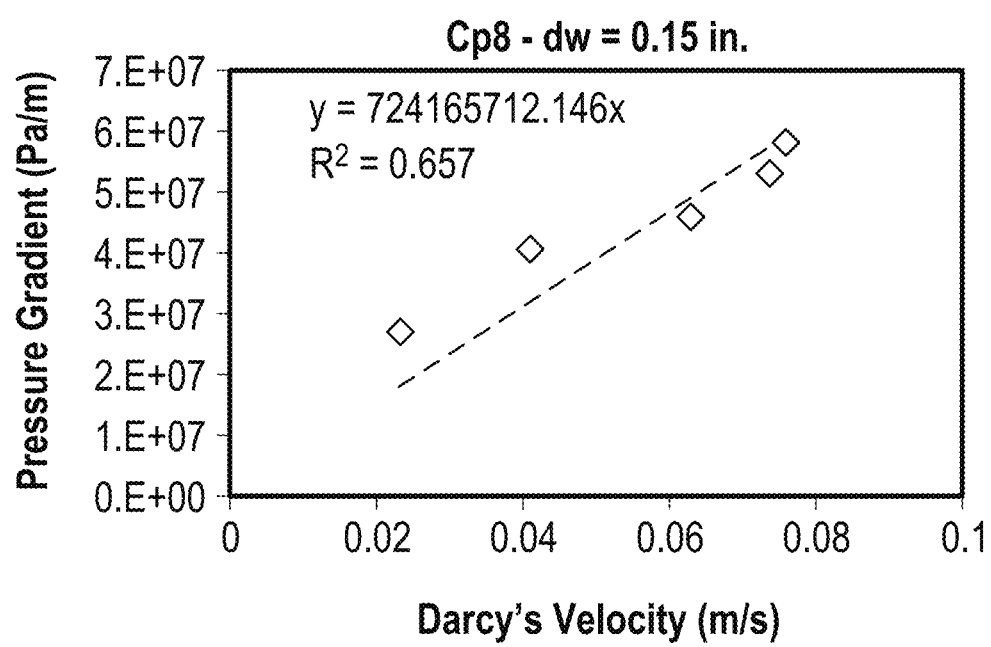

According to one embodiment, preliminary calculations of the effective permeability can be performed using the mass-flux measurements reported in FIGS. 12A-C and 13A-C to assess the impact of the probing distance on the effective permeability calculations shown in FIGS. 14A-C. Each point of the graphs in FIGS. 14A-C correspond to a different airflow rate. In this embodiment, the measurements are taken at the same location (CP8). In FIG. 14A, shown are the results corresponding to the blowing measurements collected at the prescribed distances defined by Eqs. 9 and 10, for example, $d_w=0.1$ in. for $m_{air}=10\div14$ SLPM and $d_w=0.15$ in. for $m_{air}=16\div20$ SLPM. For each condition, the hot-wire distance can be adjusted based on Eqs. 9 and 10. FIGS. 14B and C illustrate the results corresponding to the blowing measurements collected at a constant distance from the wall. In both FIGS. 14B and C, the hot-wire distance is not adjusted with the varying flow rates, but has been kept at a value of $d_w=0.1$ in. for FIG. 14B and $d_w=0.15$ in. for FIG. 14C.

A comparison between FIGS. 14A and 14B shows that the permeability results at a constant distance of $d_w=0.1$ in. from the wall provides similar results with respect to the tests performed at the optimal distances. The slope of the linear trend lines of FIGS. 14A and 14B, which are related to the permeability, differ by approximately 9%. In contrast, in the embodiment of FIG. 14C with a constant distance of $d_w=0.15$ in. from the wall, FIG. 14C shows a decrease in the correlation factor. In FIG. 14A the $R^2$ value is 0.947 compared to FIG. 14C, which has an $R^2$ value of 0.657. In an embodiment when the $d_w$ is 0.05 in., no correlation of the results was determined because the $R^2$ value less than 0.

Figure 15A:
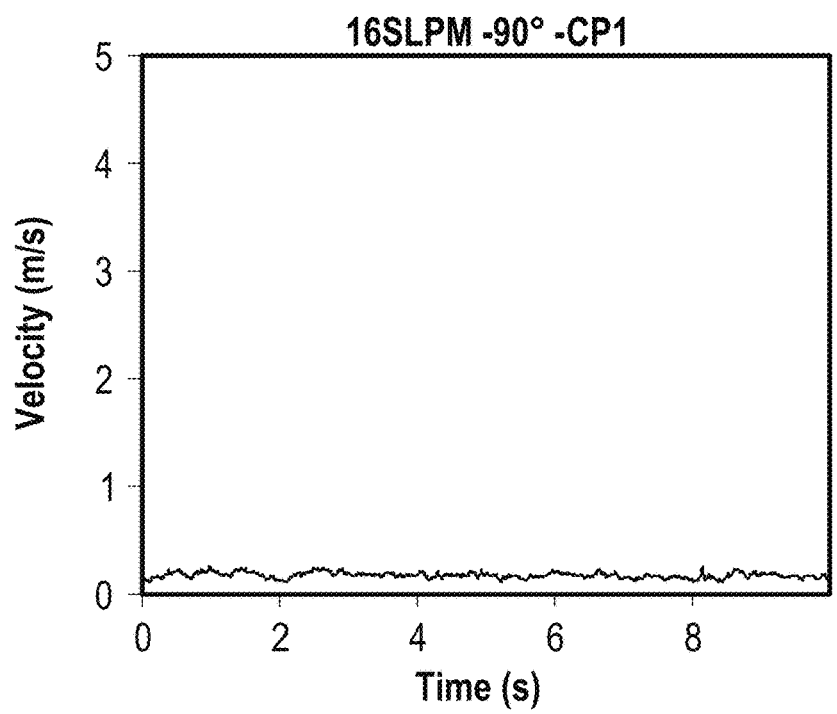
FIGS. 15A-C are graphs illustrating local velocity measurements according to various embodiments of the present disclosure.
Figure 15B:
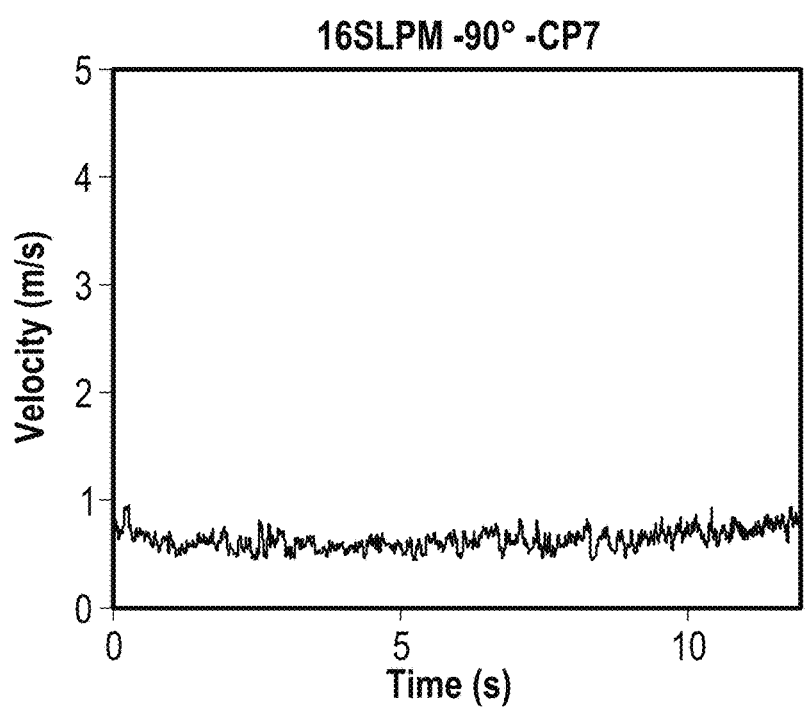
Figure 15C:
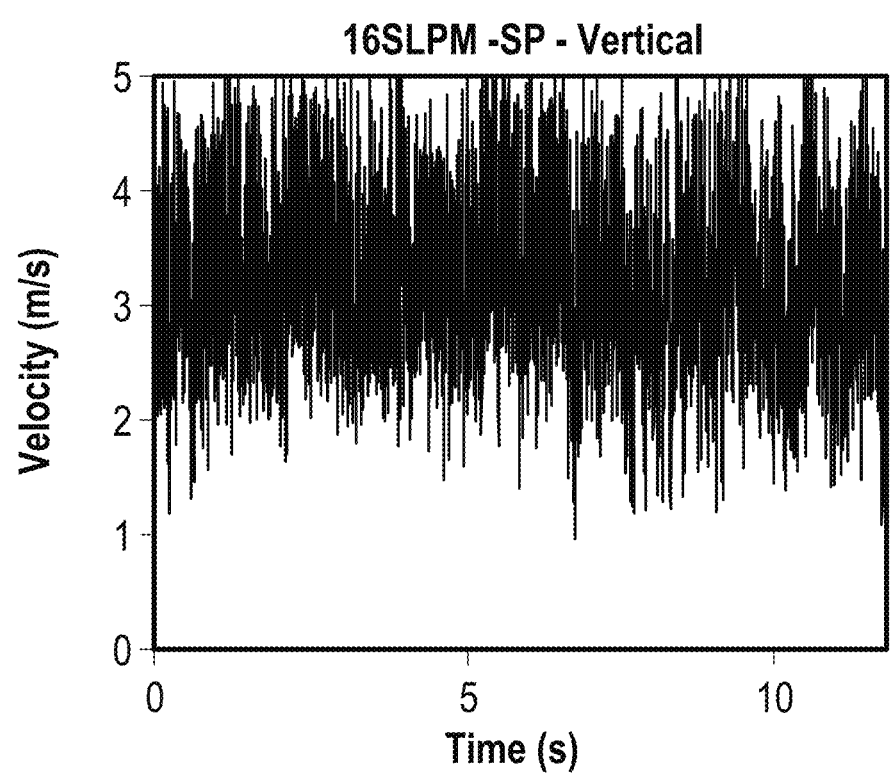
Figure 16A:
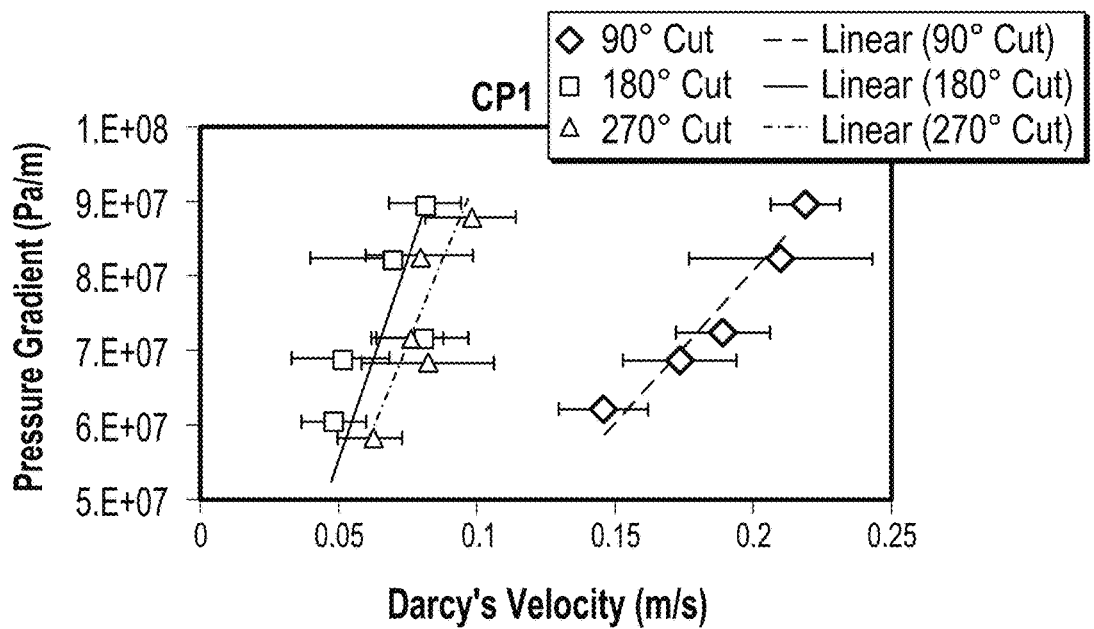
FIGS. 16A-K illustrate data at control points according to various embodiments of the present disclosure.
Figure 16B:
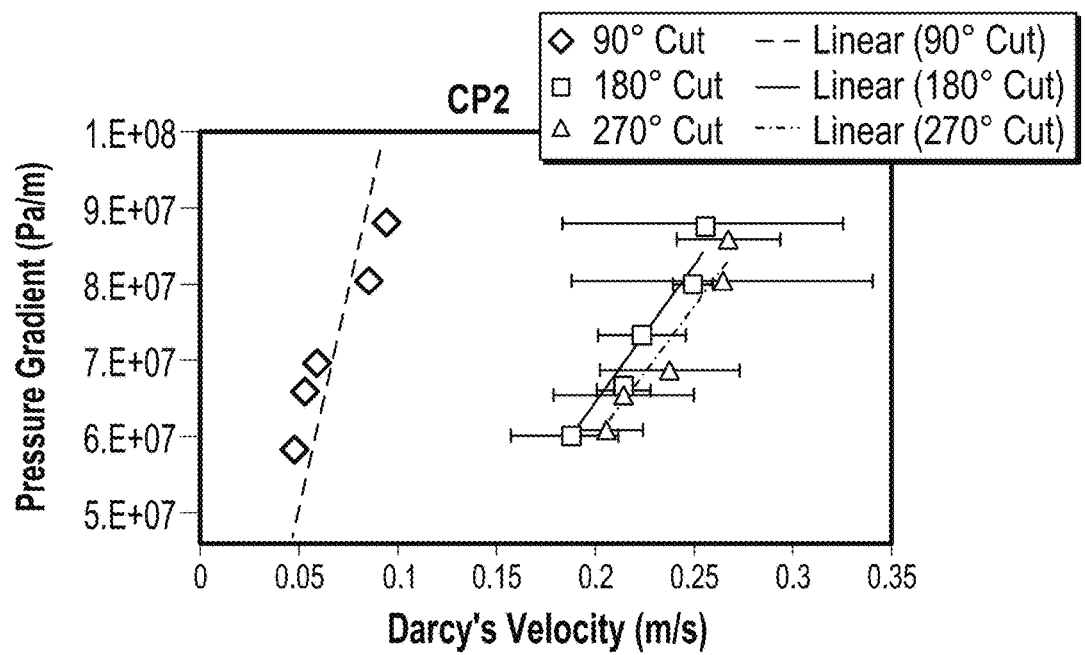
Figure 16C:
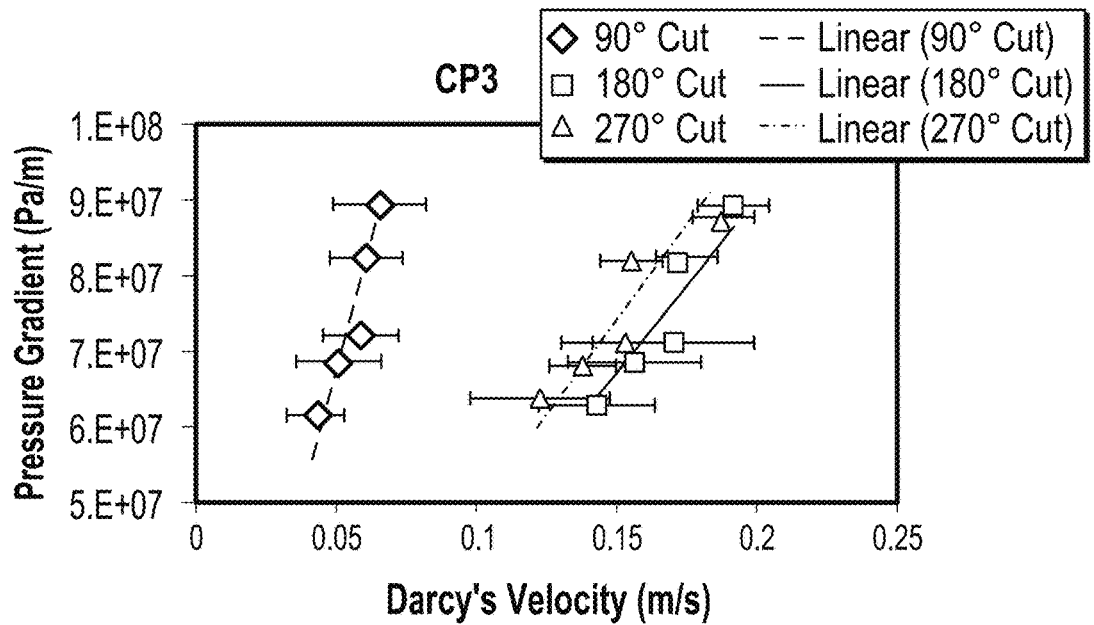
Figure 16D:
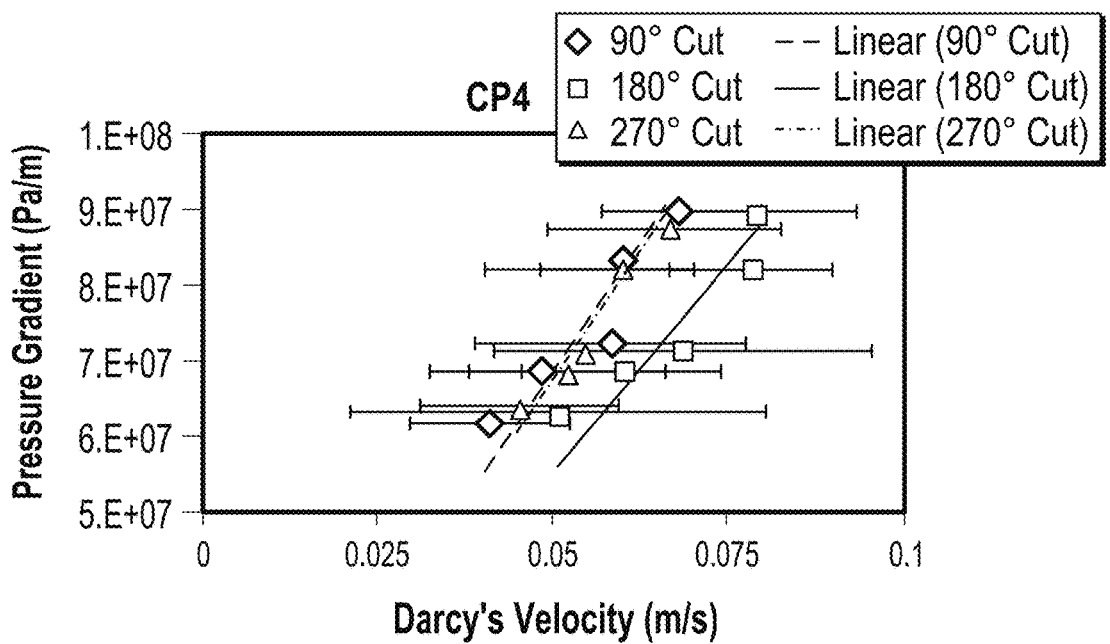
Figure 16E:
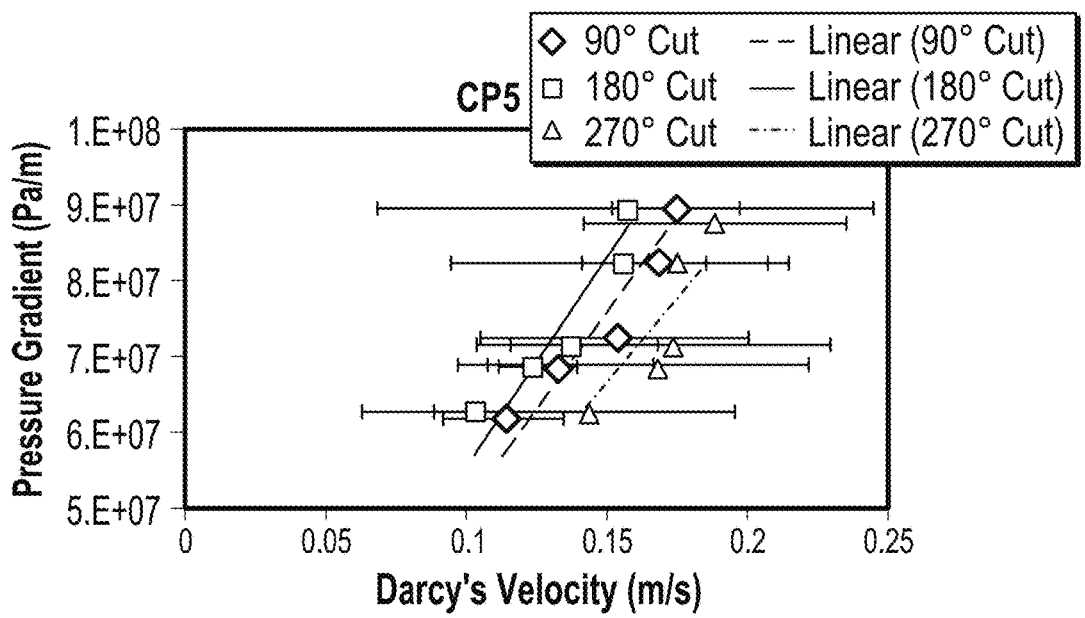
Figure 16F:
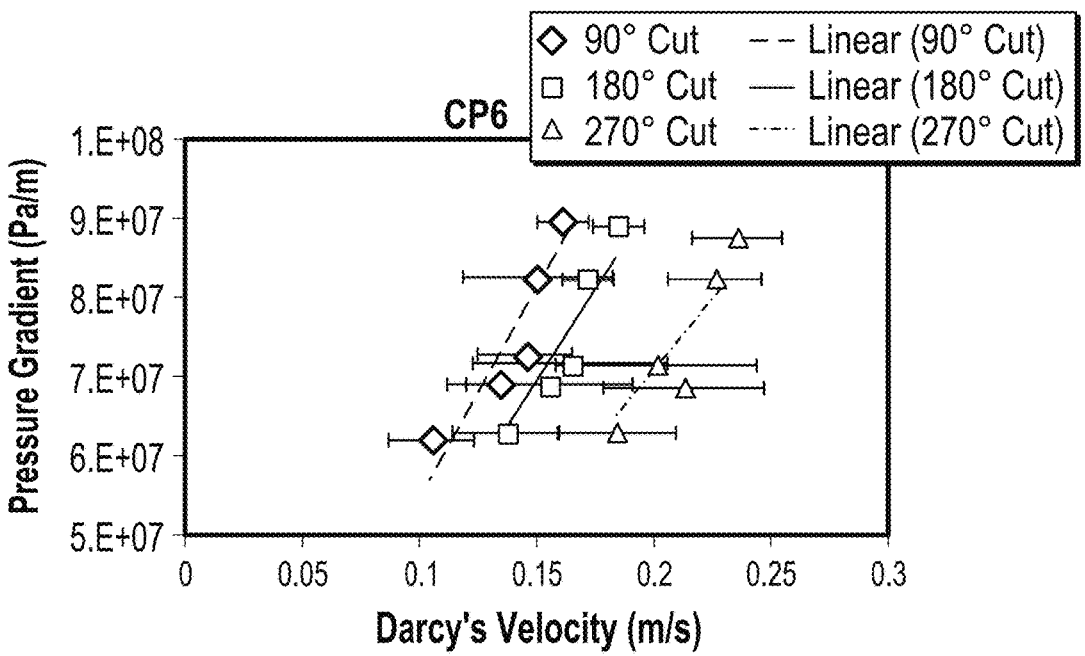
Figure 16G:
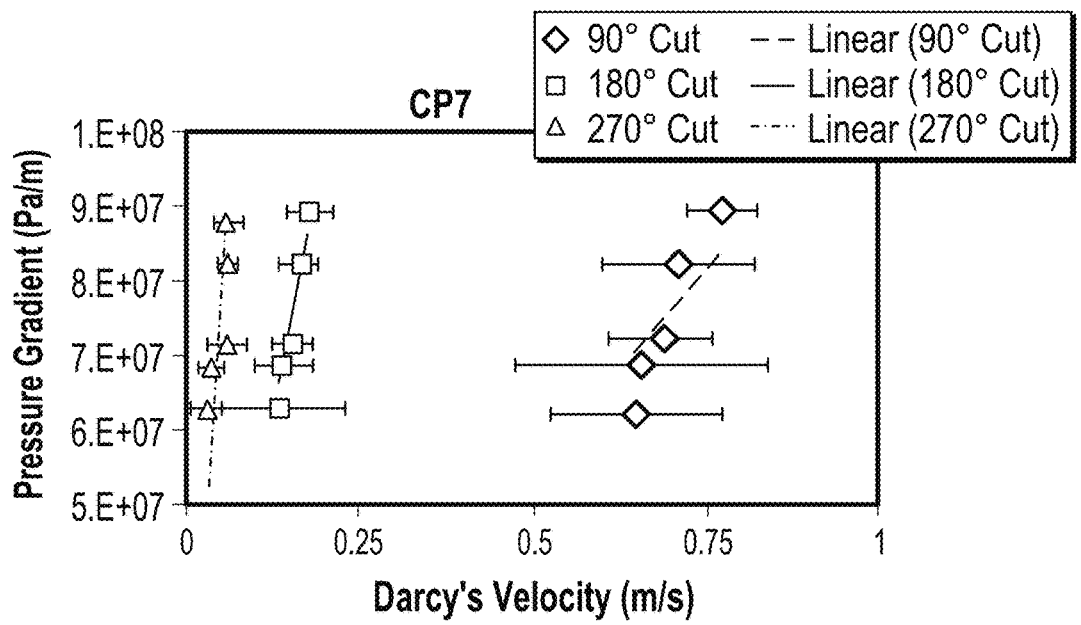
Figure 16H:
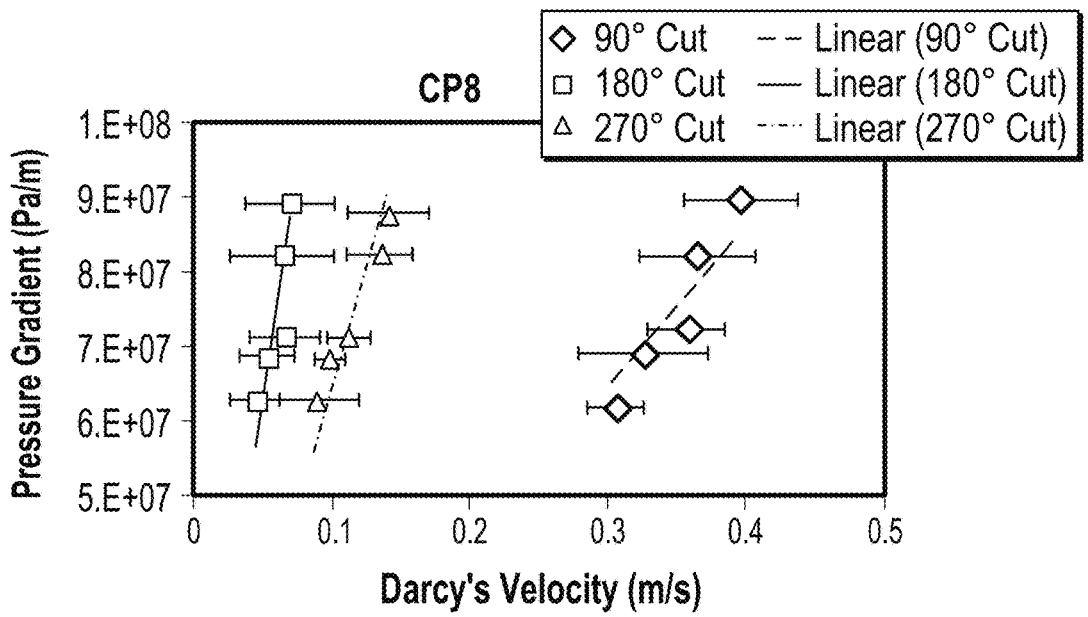
Figure 16I:
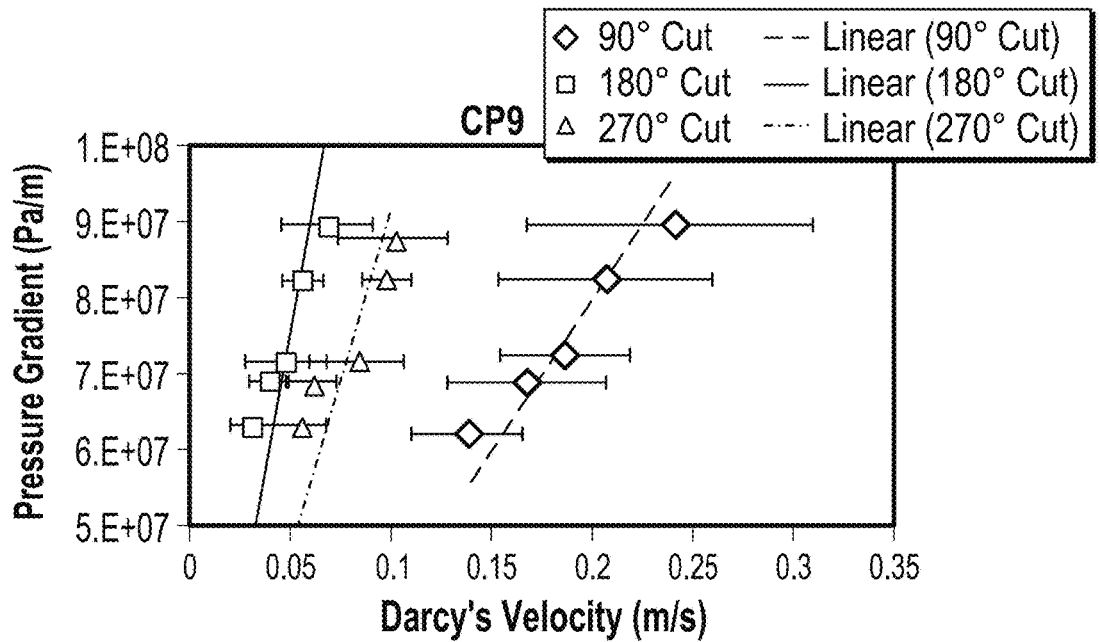
Figure 16J:
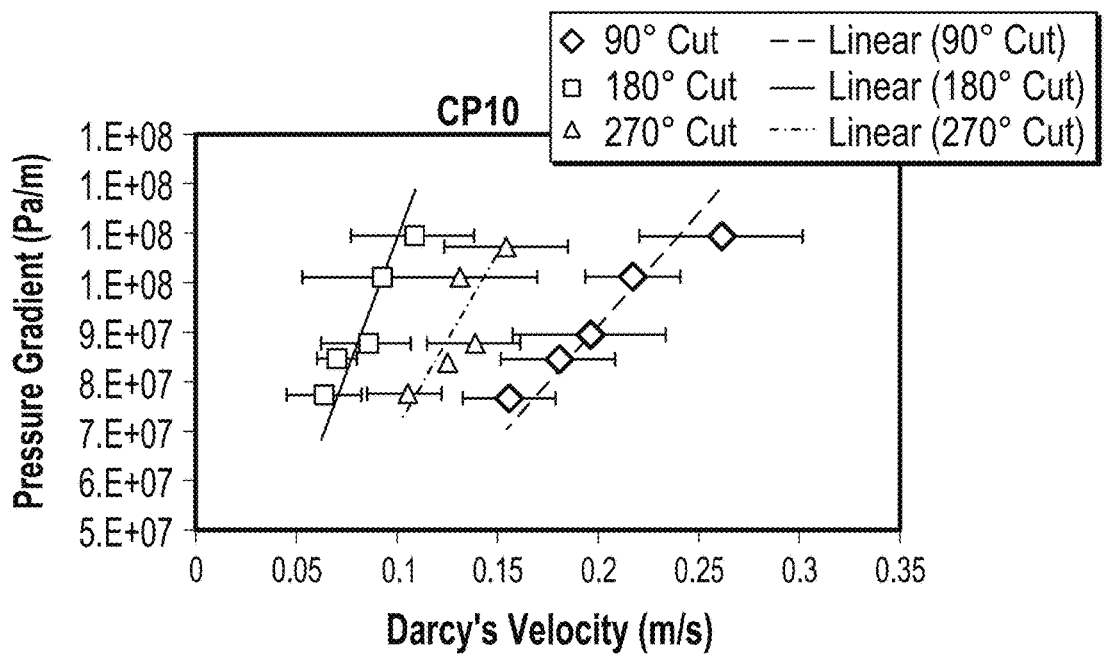
Figure 16K:
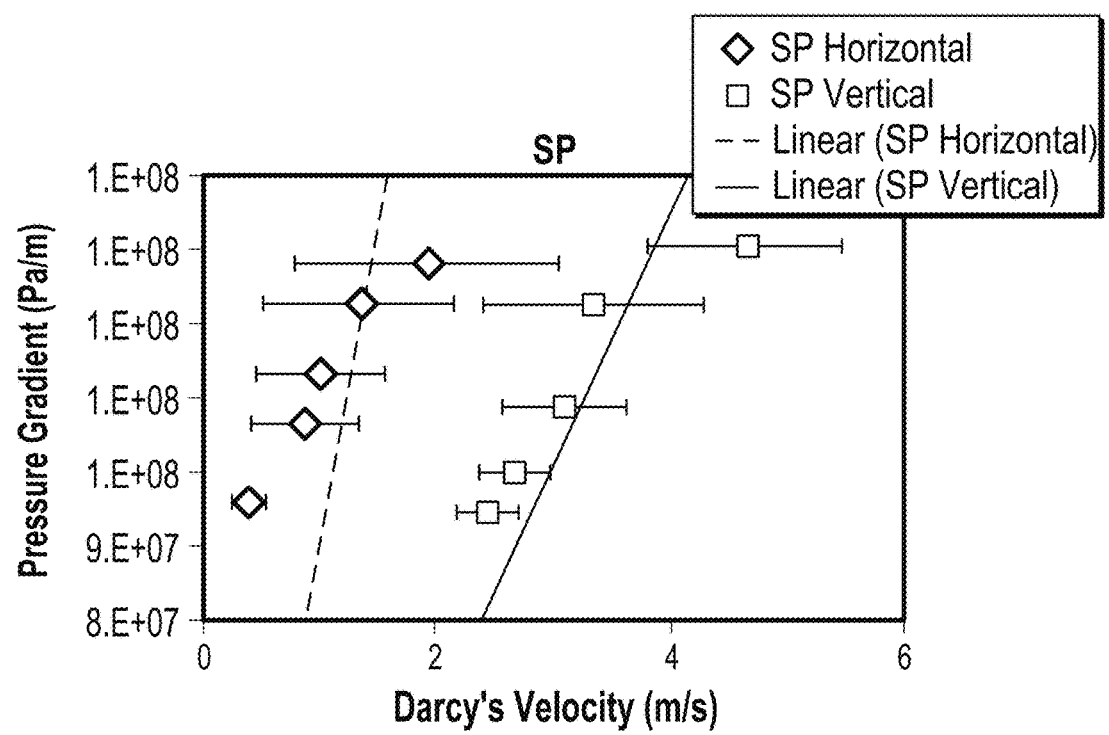

Turning next to FIGS. 15A-C and 16, shown are various graphs according to various embodiments. In FIGS. 15A-C, the graph is derived from data analysis of a hot film probing at $d_w$=0.01 in. coupled to the total pressure measurements. In FIG. 15A, shown is a lower blowing capability of the region above the truncated graphite cone because a direct feeding of coolant from the high-pressure side of the C—C material is not present. In FIG. 15B, the blowing in this region is mainly due to the radial feeding of coolant from the region above the internal plenum chamber. In FIG. 15C, the higher blowing capability of the SP region is due to presence of the radial delaminations, which can be extended along the entire length of the C—C material and can create a preferential direction of flowing for the coolant. The instantaneous velocity measurements in FIGS. 15A-C can be obtained by applying the calibration curve to the output voltages of the probe and subtracting the average background velocity in the room ($U_B \cong 0.004$ m/s) to each measurement.

Figure 9A:
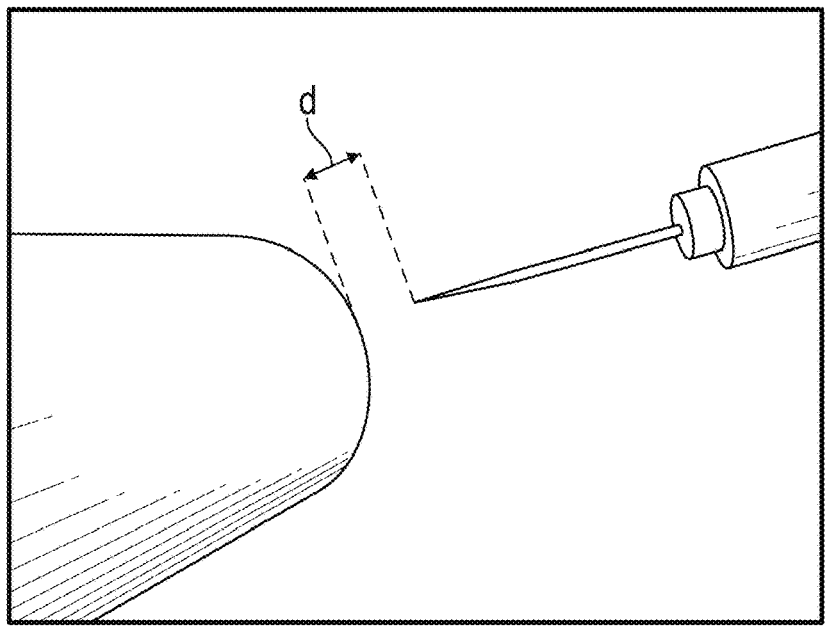
FIGS. 9A and 9B illustrate examples of horizontal and vertical probe placement according to various embodiments of the present disclosure.
Figure 9B:
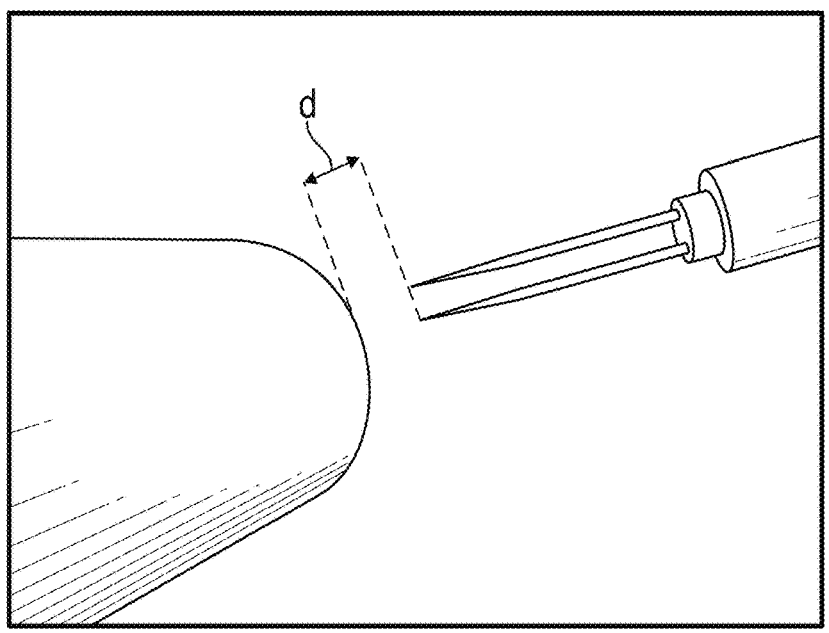

In FIG. 16, shown are graphs of the pressure gradient along with Darcy's velocity for three longitudinal sectioning planes and the five airflow rates as reported in Table 1. The velocity measurements can be conducted by placing the measuring device at the specified distance from the wall, such as, for example, as shown in Table 1. A linear curve fit using the least-squares method can be applied to reproduce Darcy's law. In FIG. 16, the linear trend lines are imposed to intercept the origin of the charts to reproduce the no-blowing condition. In this embodiment, for all the linear curve fits, the coefficient of determination is $R^2 > 0.89$, which indicates a strong correlation between the data gathered for different airflow rates at different control points. The linear fits and strong correlations verify that the permeability for this C—C material can be considered constant for the range of air flow rates used. The linear variation of the pressure drop with the velocity of the fluid measured at the low-pressure side can be caused by either, or both, the material geometry, for example, a thin-wall structure, and/or the morphology of the network of internal voids. The lower correlation coefficient can be obtained for the stagnation point probed perpendicularly to the 90-270 degree plane cut, as shown in FIG. 9A. The wider error bars on the velocity measurements for CS4 and CS5 can be caused by high fluctuations of the signal from the hot-film probe. For example, the high fluctuations can be generated by the presence of oblique jets interacting at different distances from the wall and/or the transition from laminar to turbulent jet. The transition from laminar to turbulent jet, which generates a substantial decreasing of the coalescence distance for all the flow rates used, can be produced by the presence of adjacent and bigger channels in comparison with the average network mesh size and the average diameter of the throats, respectively. The effective permeability can be calculated from Darcy's law by dividing the dynamic viscosity of air, which has been calculated using Sutherland's law at the recorded temperature, by the slope of each straight line in FIG. 16. The corresponding map of the effective permeability is reported in Table 2.

TABLE 2

Effective-permeability values for three longitudinal planes surveyed on the C-C nose tip

| | $K_{eff}^r$, mD Longitudinal cut plane | | |
|---|---|---|---|
| Location | 90 deg | 180 deg | 270 deg |
| CP1 | 34.65 ± 0.63 | 12.53 ± 0.98 | 15.04 ± 0.65 |
| CP2 | 12.93 ± 1.04 | 42.12 ± 0.70 | 44.69 ± 0.75 |
| CP3 | 10.49 ± 0.33 | 31.26 ± 0.78 | 28.52 ± 0.90 |
| CP4 | 10.28 ± 0.36 | 12.65 ± 0.41 | 10.54 ± 0.21 |
| CP5 | 27.47 ± 0.73 | 25.19 ± 0.71 | 32.03 ± 1.07 |
| CP6 | 26.09 ± 0.81 | 30.58 ± 0.78 | 40.29 ± 1.16 |
| CP7 | 129.02 ± 5.11 | 10.29 ± 0.64 | 29.39 ± 0.89 |
| CP8 | 64.94 ± 1.81 | 12.20 ± 0.52 | 21.79 ± 0.78 |
| CP9 | 34.69 ± 1.13 | 9.39 ± 0.74 | 15.39 ± 1.03 |
| CP10 | 29.72 ± 0.93 | 12.32 ± 0.56 | 19.59 ± 0.77 |
| SP horizontal | | 151.63 ± 32.4 | |
| SP vertical | | 412.58 ± 31.8 | |

The nominal values of the effective permeability can be expressed in millidarcy (1D=1.013×10$^{12}$ m$^2$) to obtain small reference numbers because millidarcy is commonly used for the analysis of porous structures in geology and petroleum applications. The average uncertainties on the effective permeability can be calculated by using Eq. 11 and ignoring the errors on the calculation of the dynamic viscosity δμ:

$$\delta K_{eff}^r = \left|\frac{\partial K_{eff}^r}{\partial a}\delta a\right| + \left|\frac{\partial K_{eff}^r}{\partial \mu}\delta \mu\right| \cong \frac{\mu}{a^2}\delta a \tag{11}$$

where a is the slope of the linear curve fits in FIG. 16. The uncertainties associated with the slope of the straight lines δa can be determined from the least-squares method. The maximum recommended percent deviations on the effective permeability are shown in Table 3. The positive and negative percent standard deviations on the effective permeability can be calculated by changing the nominal values of Darcy's velocity in relation to the error bars in FIG. 16. The range of variation of each point can be limited to those combinations that generate a coefficient of determination higher than $R^2$=0.8 to maintain Darcy's law. By limiting the maximum standard deviation for the effective permeability (Table 3), the impact of the wide error bars characteristic can be contained for CP4 and CP5 in FIG. 16.

The upper bounds of the standard deviation $\sigma^+_{K-max}$ can be referred to the lower slope of the linear curve fits in FIG. 16 (higher effective permeability). The values of $\sigma^-_{K-max}$ can be referred to the higher slope of the linear curve fits (lower effective permeability). The lower and upper bounds of the effective-permeability values can be determined using only the variation of Darcy's velocity across its error bar because of the negligible uncertainties on the pressure gradient, $\sigma_{max}(dP/dr) < 2\%$, with respect to those affecting the velocity measurements, $6\% < \sigma_{max}(U_D) < 50\%$.

Meaningful velocity measurements on the control surface along with the correct distance of the hot-film probe from the wall can generate higher impact on the nominal values of the effective permeability. The graphs presented in FIG. 16 and Table 2 allow defining the prototype material as a semi-pervious structure according to the classification based on the permeability ranges used for soils. The comparison of the nominal values of the effective permeability in Table 2 shows the asymmetric blowing capability of the C—C cone due to the conformation of the network of voids. The percent variation of the effective permeability between each plane, by considering the same control points, can range between 6% [comparison of $K^r_{eff}$ (CP2—270 degrees) with $K^r_{eff}$ (CP2—180 degree)] and 172% [comparison of $K^r_{eff}$ (SP horizontal) with $K^r_{eff}$ (SP vertical). In this embodiment, the higher permeability values are located at the stagnation point because of the two radial delaminations that create a preferential passage for the coolant fluid when a pressure gradient is applied across the wall of the material.

Intrinsic defects can be voluntarily introduced at the fabrication level with the purpose of generating an effective permeability diversified according to the cooling requirements of the TPS. According to on example, the lower effective-permeability values are not detected only for the control points above the supporting truncated cone (CP1-CP3) but rather they are distributed all over the surface because the coolant fluid flows longitudinally toward the CPs above the supporting cone. The comparison of the effective permeability for the straight-wall regions having different thicknesses (comparison of the effective permeability for CP1-CP8 with that related to CP9-CP10) illustrates that, in some embodiments, the permeability is geometrically independent (the pressure gradient is nearly constant with respect to the coolant flow rate).

Effective permeability can be used for the characterization of full-scale components/structures made of composite materials because the presence of intrinsic defects, due to, for example, the manufacturing processes, can induce asymmetric flowpaths and nonuniform heat-transfer coupling between the coolant fluid and the porous matrix. The nominal thermomechanical response of a TPS can be modified by generating concentrated mechanical loads and hot spots on the exposed surfaces.

geometric magnification used for the scan can be generated with a spatial resolution of approximately 10.6 µm/pixel for the 3-D reconstruction of the specimen. The reconstruction of the specimen can be represented by a 3-D point cloud where each point is assigned a "gray value" that ranges from zero to 65,536 and approximately represents the material density at the respective coordinate.

Figure 2B:
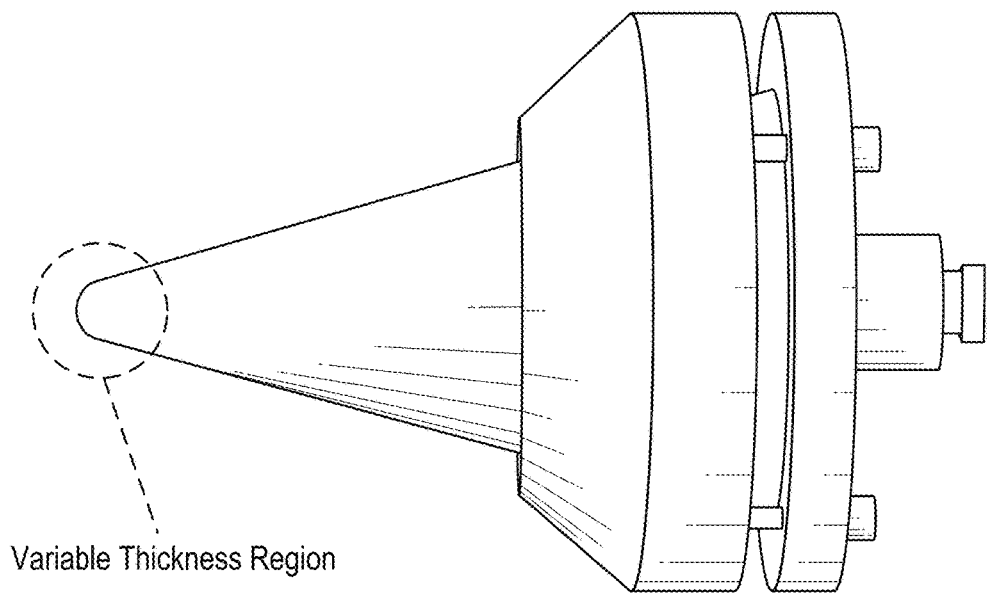

The region near the tip, characterized by a variable-thickness distribution as circled in FIG. 2B, can be scanned at the maximum achievable resolution that defines both the dimension of the smallest void structure detectable inside the material and the sharpness of the voids' contour. The 2-D segmentation of several planes, longitudinal and perpendicular to the centerline of the sample can be used for defining two parameters for performing the permeability tests by hot-film anemometry. The first parameter is the characteristic dimension of the CS where the mass flux measurements have been performed. The first parameter can be defined by a convergence criterion based on both the internal porosity, calculated from the 2-D CT scan images, and on the volumetric porosity, calculated from the 3-D digital reconstruction of the prototype sample. The second parameter is the distance of a hot-film sensor from the wall that has been calculated by using the statistical distribution of number and dimensions of the void structures across the porous lattice coupled to the average spacing of the channels.

A 3-D digital reconstruction of the cone tip can be used to calculate the average volumetric porosity ($\varepsilon_{3-D}$) and the dimensions of the reference elementary volume (REV). The influence of the probe distance from the wall can be analyzed by applying the theory of fluid flow through perforated

TABLE 3

Maximum percent standard deviation on the effective permeability

| | $\sigma_{K-max}^+$, % Longitudinal cut plane | | | | $\sigma_{K-max}^-$, % Longitudinal cut plane | | |
|---|---|---|---|---|---|---|---|
| Location | 90 deg | 180 deg | 270 deg | Location | 90 deg | 150 deg | 270 deg |
| CP1 | −6.47 | −21.27 | −11.73 | CP1 | +1.48 | +8.30 | +4.34 |
| CP2 | −18.63 | −13.91 | −7.05 | CP2 | +13.61 | +5.82 | +9.12 |
| CP3 | −19.35 | −10.01 | −9.62 | CP3 | +16.61 | +12.88 | +11.60 |
| CP4 | −15.30 | −17.73 | −19.82 | CP4 | +10.38 | +3.32 | +14.04 |
| CP5 | −20.90 | −23.48 | −15.97 | CP5 | +8.63 | +13.97 | +5.73 |
| CP6 | −8.54 | −7.00 | −9.85 | CP6 | +6.09 | +3.98 | +2.93 |
| CP7 | −4.32 | −9.62 | −18.24 | CP7 | +1.64 | +8.51 | +16.31 |
| CP8 | −5.91 | −24.53 | −14.13 | CP8 | +5.05 | +17.82 | +6.50 |
| CP9 | −19.46 | −18.40 | −20.00 | CP9 | +14.19 | +18.14 | +13.91 |
| CP10 | −10.80 | −20.69 | −15.71 | CP10 | +8.54 | +11.76 | +14.08 |
| SP horizontal | | −2.46 | | SP horizontal | | +10.70 | |
| SP vertical | | −16.30 | | SP vertical | | +13.37 | |

The assembly of the axisymmetric C—C nose shown in FIGS. 2B and 8A can be characterized. According to one embodiment, a specimen can be scanned with an x-ray CT system. This CT system can use a XWT-225-SE microfocus x-ray tube with maximum voltage rating of 225 kV, and Varian 4030E series flat panel detector. The specimen scan can be completed at 40 kV tube voltage, 600 µA target current, and the speed of 0.65 frames per second while averaging three frames per angle. The radiographs can be taken at each quarter of a degree, resulting in 1440 radiographs for the full rotation. These parameters can be selected to maximize reconstruction contrast and minimize defocusing of the tube and resulting unsharpness of the scan. A 12× plates/screens, which can facilitate identifying the range of optimal distances for the mass flux measurements. The correct probing distance can be used to obtain meaningful velocity measurements in terms of minimum fluctuations with respect to the mean velocity field, as shown in FIG. 11. In fact, in the near-wall region, single jets can be discernable with a pattern that mimics the perforated arrangement of the porous surface, whereas, at the merging distance ($L_m$), the jets can coalesce together.

Under these circumstances, the hot film can cross low-velocity and high-velocity regions with the periodicity of the pores pattern when the hot film is moved parallel to the surface at a distance $r<L_m$. The velocity fluctuations can increase consistently at the merging distance ($r=L_m$), whereas for r slightly higher than the merging distance, a near-continuous blowing velocity can be detected. The merging length can depend on the network-mesh size (M) and on the Reynolds number based on the channels' diameter ($Re_{ch}$). Specifically, below a certain critical Reynolds number ($Re_{cr} \approx 20$), the spreading angle of the jets decreases with the Reynolds number and the merging distance follows the relation $L_m \sim M \cdot Re_{ch}$. When $Re_{ch} > Re_{cr}$ (turbulent jets), the spreading angle of the jets can increase with $Re_{ch}$ and the merging distance can change its dependence with respect to the Reynolds number ($L_m \sim M \sim Re_{ch}^{-1}$).

The results derived from the analysis of the CT scan images can be used to define the guidelines needed for the correct execution of the permeability tests by using hot-film probes. A preliminary analysis can be performed to assess the most suitable contouring method necessary to calculate both the internal porosity by analyzing 2-D images ($\varepsilon_{2-D}$) and the volumetric porosity ($\varepsilon_{3-D}$). Both the average porosity values can be used to infer the minimum dimensions of the area to be probed, whereas the analysis of distribution and dimension of the internal voids' structure can be used to estimate the correct distance of the sensing film from the wall.

Figure 17A:
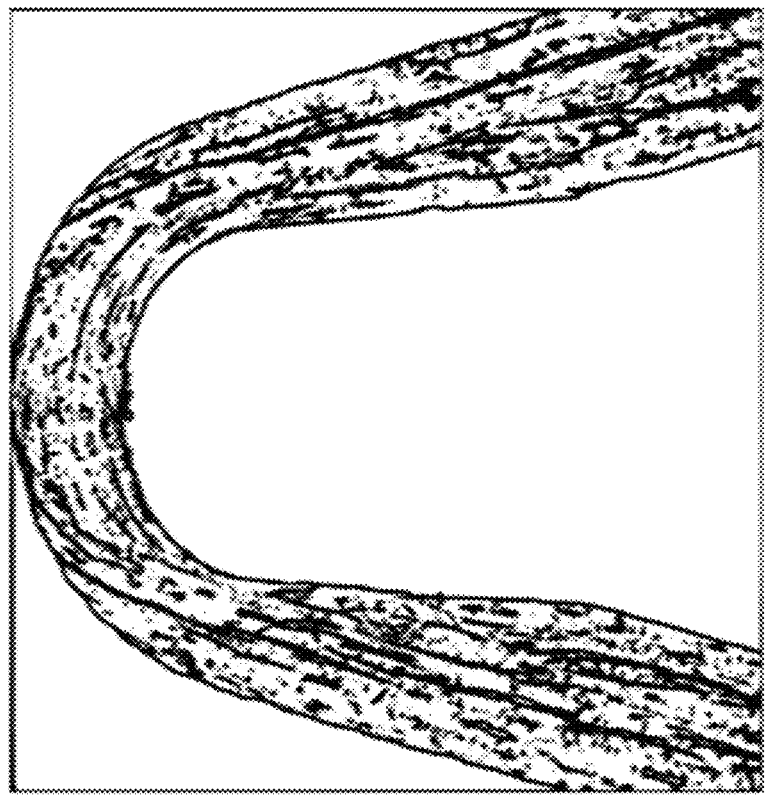
FIGS. 17A-B illustrate longitudinal cuts according to various embodiments of the present disclosure.
Figure 17B:
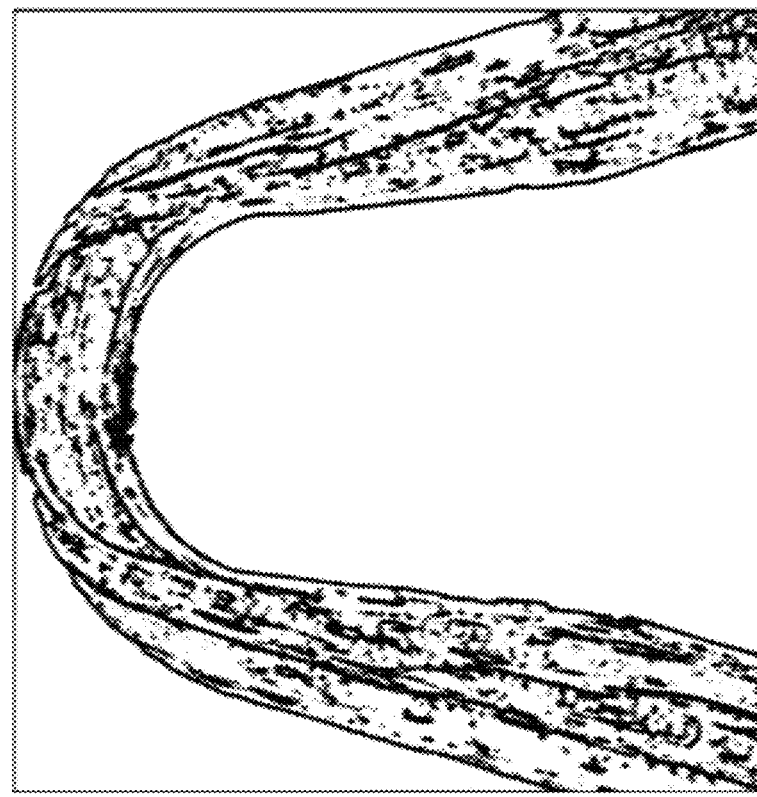
Figure 18C:
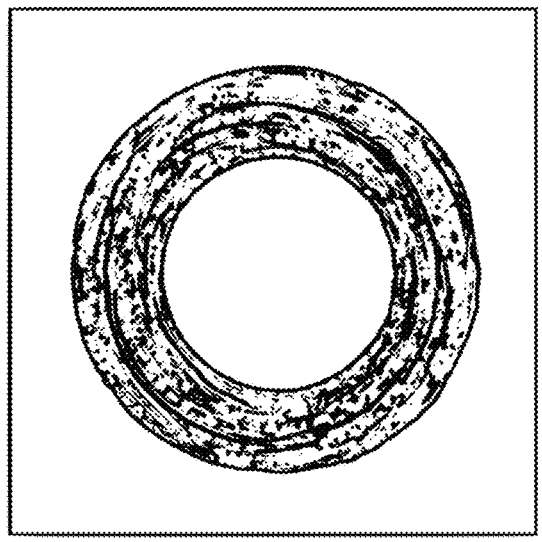
FIGS. 18A-C illustrate transversal cuts according to various embodiments of the present disclosure.

Several longitudinal sections can have variable span angles as shown in FIG. 17 and transversal cut planes as shown in FIG. 18. These longitudinal sections can be analyzed to calculate the 2-D porosity of the specimen. An automatic procedure can be used to calculate the void-to-material ratios once the interrogation area and the contouring method for the images have been selected. An annulus region can have a radius that changes accordingly to the variation of the specimen's thickness. The annulus region can be used as the interrogation area for the transversal cut. The interrogation area for the longitudinal cut can exclude the regions very close to the tip of the samples because of an out-of-focus blemish. The nominal value of the gray-scale threshold, under which the presence of an empty structure, typically containing air, can be determined for the analysis of the 2-D images by selecting three threshold selection methods (TSMs) named: minimum, OTSU, and moment TSMs.

These methods can be characterized by employing different thresholding/contouring categories and can be used in several research fields (e.g., geology, medicine, engineering, etc.) to identify density variations across homogenous and nonhomogeneous media. For example, the methods can be used in petroleum engineering for the calculation of the natural porosity of soils (unconsolidated media) and porous rocks (consolidated media). The use of the above mentioned methods for aerospace applications is relatively new and of particular interest because of the growing use of composite materials that have to be characterized at the full-scale level, by using non-intrusive techniques, due to their intrinsic defectology introduced during the manufacturing processes. The minimum method belongs to the histogram shape-based thresholding methods for which the background and foreground pixels are detected based on the peaks, valleys, and curvatures of the gray-levels histogram.

The OTSU method belongs to the clustering-based contouring methods, where the gray values are clustered separately in foreground and background classes and the optimum threshold value is computed in order to minimize the weighted sum of within-class variances. The moment method belongs to the attribute-similarity contouring methods that implement an algorithm to search for a measure of similarity between the gray-level image, considered the blurry version of an ideal binary image, and the binarized image.

Figure 19:
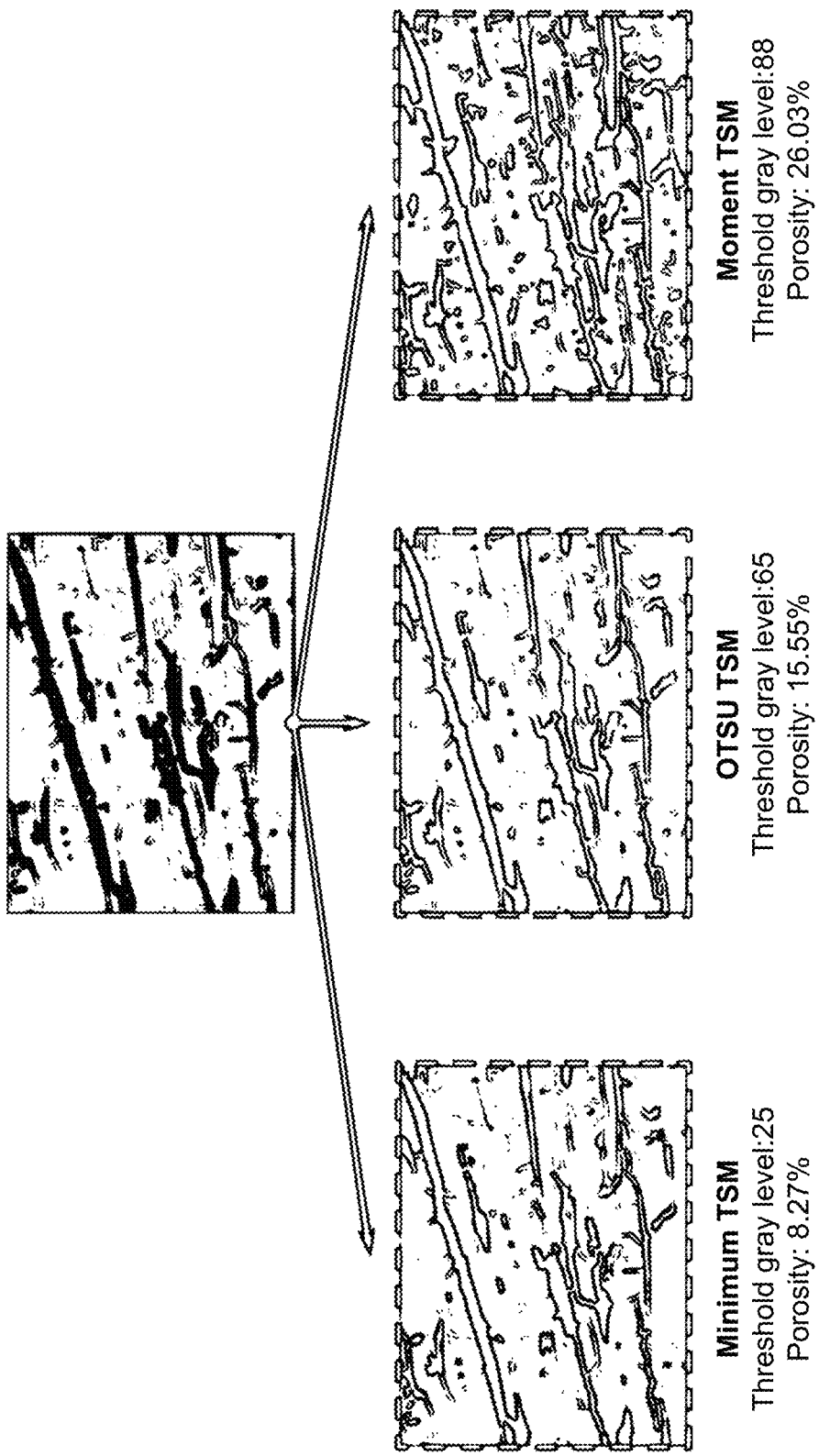
FIG. 19 illustrates different thresholding methods being applied to a portion of an example material according to various embodiments of the present disclosure.

FIG. 19 shows an example embodiment of the same portion of material analyzed by the aforementioned TSMs. The minimum TSM underestimates the real porosity because the low value of the threshold gray level prevents considering the smaller channels for the computation of the void-to-material ratio. Conversely, the moment TSM overestimates the real porosity because the higher threshold value computed takes into account all of the entities having a gray-tone slightly darker than the solid material. The darker spots are not necessarily empty spaces, but the darker spots can represent density changes across the carbon matrix and, thus, the darker spots are not relevant for the porosity calculation. Additionally, the high value of the threshold gray level substantially increases the boundaries of the real cavities creating extended defects. In this perspective, the OTSU method can be used to provide the reference gray-level threshold necessary to calculate the internal porosity of the sample from 2-D images ($\varepsilon_{2-D}$). In fact, the OTSU method can be used when working with images having extremely defined peaks in the gray-levels histogram.

The uncertainties on the porosity of each cut can be calculated by moving the optimal threshold, estimated by the OTSU method, of few counts (+ or −5%) in order to include some minor voids detected by visual inspection of each single image. The 3-D reconstruction of the prototype sample can be used to independently calculate the average volumetric porosity ($\varepsilon_{3-D}$). The transverse slices of the nose tip can be used for the calculation of the volumetric porosity by selecting the coordinate of one point on the transversal plane and by extending the third direction accordingly to the side dimension of the volume considered. The transversal sectioning planes, stacked for the computation of the void-to-material ratio, can be selected to maximize the number of extractions from the probing volume. The resulting spacing can be approximately 10.6 μm.

Two contouring methods can be used to determine the optimal threshold for the 3-D digital reconstruction: the K-means TSM (similar to the OTSU TSM) and the mean density TSM. The optimal threshold value for the K-means method can be assessed to be gray level 5104 of the total 65,536 gray levels available, whereas the gray level 5125 can be found to be the optimum threshold value for the mean density method. The mean density TSM allowed assessing also the variation in the threshold definition by finding noisy variation of the air (+ or −10) and material gray values (+ or −40), resulting in the acceptable threshold variation from 5100 to 5150.

Figure 20:
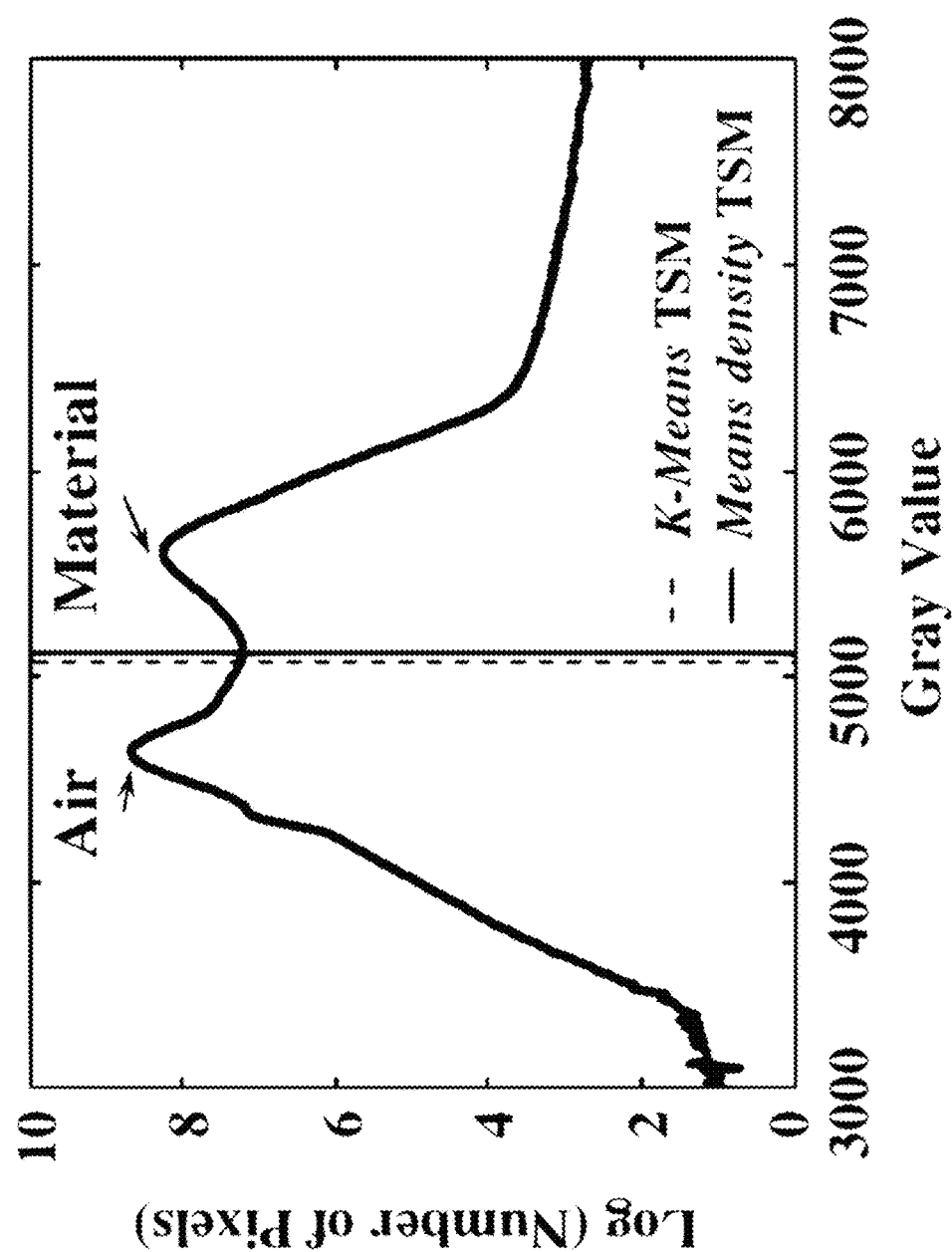
FIG. 20 is a graph of a gray-level histogram of a region of a material according to various embodiments of the present disclosure.

FIG. 20 shows an example zoomed-in image of the gray levels histogram of the scan with the optimum threshold values determined by the previously mentioned algorithms. The calculated average volumetric porosity values are reported in Table 4. Table 4 shows that the volumetric porosity calculated from the 3-D reconstruction provides slightly different results with respect to nominal porosity calculated from the 2-D sections.

TABLE 4

Average volumetric porosity calculated by two additional contouring methods

|  | Constant-thickness region | Variable-thickness region | Tip region |
|---|---|---|---|
| $\varepsilon_{3\text{-}D}$ (K-means TSM) | 10.4% | 10% | 9.5% |
| $\varepsilon_{3\text{-}D}$ (Mean density TSM) | (11.1 ± 6.3)% | (10.5 ± 4.8)% | (9.9 ± 7.0)% |

In fact, the internal porosity calculated from a discrete number of longitudinal and transversal cuts ($\varepsilon_{2\text{-}D}\cong14.6\%$) is higher than the volumetric porosity ($\varepsilon_{3\text{-}D}\cong10.5\%$) by 39%, if the mean density is considered. The deviation between the two independent calculations is mainly due to the different total number of gray levels considered. The 256 gray levels used for the analysis of the 2-D images (8-bit pictures) allow detecting only one peak in the histogram. The 65,536 gray levels used for the analysis of the 3-D reconstructed domain allow distinguishing two peaks (FIG. 20) that sharply separate the background pixels (air) from the foreground pixels (material). However, the deviation in terms of nominal porosity does not affect the results in terms of dimensioning of the probed area because the analyses of the reference elementary surface (RES) and REV provide analogous results.

The dimension of the CS can be based on the size of the characteristic area that facilitates obtaining meaningful local measurements in terms of minimum mean velocity fluctuations. The mass flux measurements, obtained by using hot-film anemometry, can be associated to selected control points (CPs) which corresponds to measurements collected at the center of the correspondent CS. Squared probing boxes, generally of different dimensions, can be used to survey different areas of a CT scan images and, thus, to define the RES by detecting a plateau of the porosity plot. A reference dimension, coincident with the spatial resolution of the CT scan (10.6 μm/pixel), can be applied to each image with the purpose of defining the nominal dimensions of the probing surfaces. The pixels-to-inch conversion scale can also be used to verify the nominal variation of the specimen thickness prescribed at the design stage.

According to one embodiment, both the plane sections having higher and lower porosity present similar characteristics in terms of porosity's convergence for a probing surface of 0.09 in×0.09 in: The maximum variance of the porosity with respect to the average value is about 8% (lower-porosity plane) and 6% (higher-porosity plane) for the probing surface. Additionally, the nominal values of the porosity for the larger probing surface can be within the range of porosity values calculated on the entire conical profile of the nose tip. Similar results in terms of RES can be obtained for the transversal cut. The same procedure can be applied to calculate, independently, the REV by defining cubic volumes having a side dimension varying from 0.02 to 0.08 in. One hundred 3-D coordinates distributed in selected transversal planes of the nose tip can be used for the calculation of the REV.

Figure 18B:
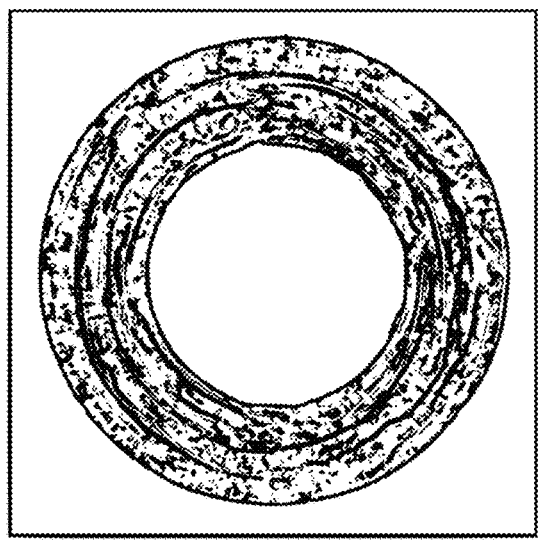
Figure 18A:
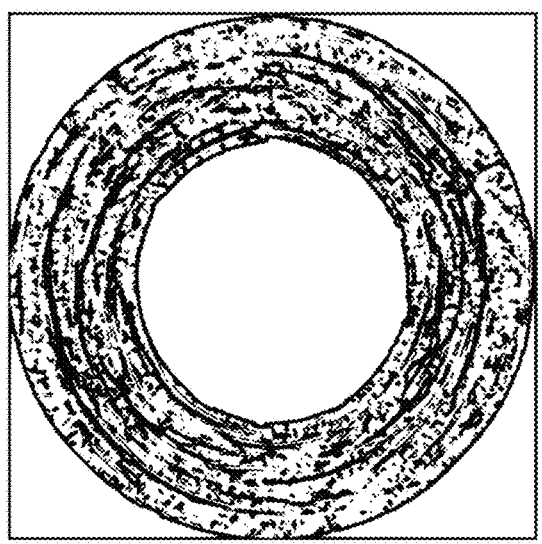

In one embodiment, the calculated volumetric porosity does not show a monotonic convergent trend because it starts increasing for side dimensions bigger than 0.08 in. In this embodiment, the side dimensions of the cubic volume bigger than 0.08 in. are not considered for the REV calculation because the side dimensions exited from the borders of the nose tip and, thus, the probing volume started to capture areas outside the shape of the cone with the consequent over-prediction of the void-to-material ratio. This geometrical issue can be overcome, for the RES calculation, by shaping the reference surfaces around the curved borders of the cone. The REV determination starting from the transversal cut of a constant-thickness region (FIG. 18A) and a variable-thickness region (FIG. 18B).

Similar trends in terms of porosity distribution can be seen for the square surfaces and the cubic volumes selected. The maximum variance of the volumetric porosity with respect to the average value is about 33% and about 40% for an example probing volume. In some embodiments, higher scattering of the data from a 3-D sectioning can be attributed to a high anisotropy of a tortuous structures that connects void elements characteristics of consecutive sectioning planes. A squared CS having the dimensions of $D_{CS}$=0.1 in. can be selected to survey the blowing capability of the prototype cone by obtaining meaningful velocity measurements ($D_{CS}\geq\max(D_{RES};D_{REV})$) and by maintaining, at the same time, a high spatial resolution ($D_{CS}$ as small as possible).

A hot-film probe can be used to confirm the statistical steadiness of the mean velocity field measured across the CS for all locations and flowrates used. The control surface can correspond to a region above an internal plenum that has variable thickness (FIGS. 2A and 8B). The variation of the mean velocity across the CS, for all the probed locations and flow rates used for a preliminary test campaign, can range between 0.5 and 4.8%. For this reason, the mass flux measurements can be collected at the center of the CS and, thus, can be related to the CPs.

Statistical analysis of the voids' distribution inside the C—C specimen can be used with the aim of defining the porosity of the external surface (superficial porosity, $\varepsilon_{sup}$) and the characteristic dimension of the channels. The former can be used to calculate the local flow velocities (seepage velocity, u), whereas the latter can be used to define the Reynolds number for determining the flow regime and, thus, to estimate the coalescence distance of the jets. The variation of the Reynolds number along the specimen sidewall, which is due to the different blowing capability of the TPS structure, can be used to define the flow regime and, thus, to justify the use of the Darcy's law for the calculation of the effective permeability.

In addition, the statistical characterization of the empty structures inside the porous sample can be used in support of numerical modeling for the thermomechanical response of porous structures by using the equivalent medium theory. The analysis of only the 2-D longitudinal and transversal sectioning planes can be used for the statistical description of the porous media because the analysis can provide results fairly in agreement with the analysis of the 3-D reconstruction. In a first step of the statistical description of the porous specimen, different network elements can be recognized and classified in base of their characteristic length scales. In particular, for consolidated fibrous/layered materials, the porous lattice can be subdivided in a series of channels/throats, pores, and caverns/chambers.

The channels can be defined empty spaces having a low aspect ratio (length/diameter) combined to the lower diameter within the porous network, whereas the pores can be void structures connecting two or more channels. The pores can be distinct from the channels because of their higher diameter. The average number of channels converging to a single pore can be referred to as a coordination number (C) of the porous structure. The caverns, which for layered materials can be identified as delaminations, can be defined as empty structures having the higher aspect ratio within the porous network.

The threshold values that facilitate classifying the voids based on their length scales can be set once the network elements have been clearly identified by visual inspection of the CT scan images. The length scales thresholds selected for this study are reported in Table 5.

TABLE 5

Length scales separation for the void elements constituting the C-C nose tip

| Network elements | Channels/throats | Pores | Chambers |
|---|---|---|---|
| Aspect ratio (L/D) | <30 | <30 | >30 |
| Diameter (D) | <40 µm | >40 µm | ND |

The statistical analysis of the distribution and size of the network elements inside the full-scale specimen can be performed, once the length scales separation in Table 5 are adopted. Two annular caverns of about 65 µm thickness can extended along the entire cone tip and can be detectable for almost all the longitudinal and transversal cut planes analyzed. The throats' diameter, the pores' diameter, and the pores' length can be shown to be centered on an average value. It indicates the possibility to model the highly anisotropic internal porous structure with an equivalent medium composed of slots (equivalent to the caverns) cylindrical channels and pores.

In one example, the throats' length, which can be measured by following the tortuous paths of the channels, shows a higher variance with respect to the dimensions of the other network elements. The higher data scattering of the throats' length can be due to either, or both, the variable thickness of the specimen and/or the enhanced channel length due to the tortuosity ($\tau = l_t/l_{st}$). Here, the influence of the latter can be neglected because the tortuosity for both the transversal and the longitudinal cut planes, which can be calculated based on a limited count of hundred samples of the channels, can be nearly constant to $\tau = 1.32 +$ or $-0.1$.

In addition, a left region of the throats' length (0<Samples<80) can correspond to the tip region (lower thickness), whereas a right region of a throats' length (80<Samples<140) can correspond to the variable- and constant-thickness region. These results can open the scenario of using an equivalent medium having a variable channel's length that is proportional to the thickness variation. However in one embodiment, only the statistical distribution of voids' diameter is reported for the purpose of defining both the Reynolds number and the porosity of the external surface. The average diameters, along with the standard deviations of the throats, pores, and caverns, can be used in a normal distribution function with the scope to verify if the average diameters provided a good representation of the statistical distribution of the network elements.

Both the throats' and the pores' diameters can follow the Gaussian distribution centered on the average diameters. The probability density function of the pores' diameter can be wider with respect to the one that referred to the throats' diameter because of its higher relative scattering of the data. The same analysis can be performed for the lengths of the void structures with the purpose of defining the equivalent model for the internal structure of the porous material. The number of empty structures inside the RES can be estimated by analyzing a few longitudinal and transversal cut planes and avoiding the out of focus regions (Table 6). Table 6 shows that the number of void structures across the material thickness can be approximately equal for longitudinal and transversal cut planes. The uncertainties can be calculated starting from the standard deviations on the counts of the void elements for each longitudinal and transversal sectioning plane.

TABLE 6

Average number of voids elements per unit RES

| Network elements | Longitudinal throats | Radial throats | Pores | Chambers |
|---|---|---|---|---|
| Average counts (longitudinal cuts) | 12.3 ± 4.9 | 24.8 ± 3.3 | 11.8 ± 2.1 | 1.8 ± 0.4 |
| Average counts (transversal cuts) | 12.8 ± 3.1 | 22.0 ± 3.5 | 10.0 ± 2.1 | 2.0 ± 0.1 |

The distinction between longitudinal throats (x direction in FIG. 2A and radial throats (r direction in FIG. 2A) can be used to define the average number of void structures that reach the free boundaries and, thus, to estimate the superficial porosity. Only a certain quantity of all the radial throats detectable per unit RES, ranging between 6 and 8 elements, can reach the external surface for both the longitudinal and transversal segmentations. A circular cross section for the throats can be assumed due to the statistical absence of channels extension in the third dimension when two contiguous sectioning planes (1 degree spacing) are analyzed. At this stage, the external porous surface of the cone can be modeled in order to estimate the superficial porosity ($\varepsilon_{sup}$) and, thus, to calculate the Reynolds number based on the channels' diameter. In particular, the CS can be schematized as a perforated flat surface having uniform porosity that is determined by both the average channel's diameter and by the average number of channels reaching the external surface.

The curvature of the outer surface of the specimen can be neglected due to the small dimensions of both the CS and the interrogation area of the hot film compared to the overall external diameter of the C—C mask. The porosity of the external surface can be estimated by applying the previously mentioned model based on a perforated plate having a variable number of circular channels per side of the CS (6<counts$_T$<8). The average diameter of the channels, $D_{ch}=$ (29.47+ or −5.57) µm, can be imposed based upon the results deriving from the statistical distribution of the voids' diameter (FIG. 12). The resulting superficial porosity is $\varepsilon_{sup}=$ (0.5+ or −0.1)%.

Figure 21:
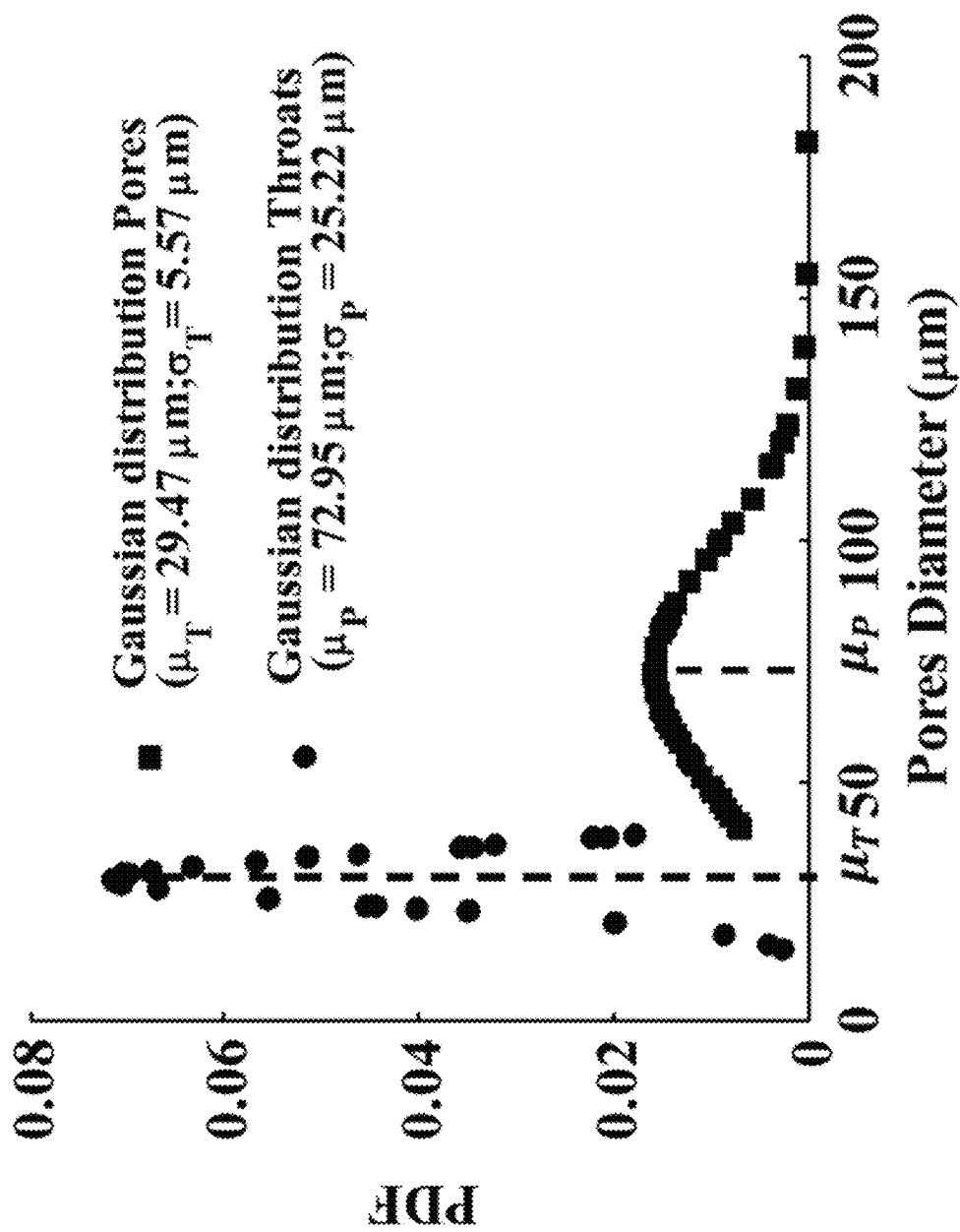
FIG. 21 is a graph of a probability density function corresponding to a Gaussian distribution for diameters of throats and pores according to various embodiments of the present disclosure.

The combined use of the average throats' diameter reported in FIG. 21 and porosity of the external surface ($\varepsilon_{sup}$) can facilitate estimating the Reynolds number with the purpose of assessing the range of variation of the coalescence distance of the jets. Thus, the distance of a hot-film probe for permeability tests can be correctly defined. Additionally, the statistical characterization of the internal structures of the porous material can be used to determine the range of variation of the network-mesh size (M). The coalescence distance of the jets can be estimated by using the CT scan images of the cone coupled with preliminary velocity measurements obtained by placing the hot-film probe at $d_w=0.05$ in: from the wall with the scope to quantify the range of variation of $Re_{ch}$. The merging distance for the selected specimen can change along the specimen sidewall because the blowing velocity and, thus, the Reynolds number based on the channels' diameter can be variable. An estimate of the minimum and maximum merging distance of the single jets from the porous wall can be given by Eqs. 9 and 10, respectively.

The minimum and maximum network-mesh sizes measured from the 2-D CT scan images can be $(M)_{min}$~0.012 in. and $(M)_{max}$~0.014 in, respectively. The Reynolds number ($Re_{ch}=(U_D D_{ch})/\varepsilon_{sup}\nu$)) can be estimated from the preliminary velocity measurements of the hot film (UD) obtained for selected CPs in FIG. 8B and from the average diameter of the channels as shown in FIG. 21 ($m_{air}$=0.26 g/s, $(Re_{ch})_{min}$=4; $m_{air}$=0.43 g/s, $(Re_{ch})_{max}$=13). Both the lower and the higher flow rates used for the permeability tests (Table 1) can be imposed to determine the range of variation of the Reynolds number. Additional blowing tests, using air as working fluid, can be performed at prescribed distances from the wall to verify the overall prediction on the average coalescence distance of the jets.

The coalescence distance, as predicted by Eqs. 9 and 10, can be increased with the imposed air flow rate. The closest distance of the probe from the wall for the range of flow rates considered can produce standard deviations on the transversal wall velocity values larger than the nominal value of the mean velocity ($\sigma_U > U_D$). The correct probing distance for 10 SLPM<$m_{air}$<14 SLPM can be around $d_w$=0.1 in. because the standard deviation on the velocity measurement is lower than 50% with respect to the mean velocity. The farther distance from the wall is not suitable for the permeability tests because of the natural velocity decay far downstream the coalescence distance of the jets.

The correct probing distance for the remaining flow rates used ($m_{air}$=16÷20 SLPM) is around $d_w$=0.15 in. The highest velocity fluctuations detectable can be determined by the capturing of the merging location of coflowing jets where local instability of the flow is generated. The comparison of the experimental results with the predictions, obtained via Eqs. 9 and 10, can corroborate the validity of the methodology used to define the range of variation of the optimal hot-film distance from the porous wall. Preliminary calculations of the effective permeability can be performed using the mass flux measurements to assess the impact of the probing distance on the effective permeability calculations (FIG. 14A-C). Each point of the graphs in FIG. 14 can correspond to a different airflow rate. All the measurements have been taken at the same location (CP8).

FIG. 14A shows the results corresponding to the blowing measurements collected at the prescribed distances defined by Eqs. 9 and 10 (i.e., $d_w$=0.1 in. for $m_{air}$=10÷14 SLPM and $d_w$=0.15 in. for $m_{air}$=16÷20 SLPM). For each condition, the hot-wire distance can be adjusted accordingly. FIGS. 14B and 14C report the results corresponding to the blowing measurements collected at a constant distance from the wall. Specifically, in both cases, the hot-wire distance was not been adjusted with the varying flow rates but was kept at a value of $d_w$ 0.1 in. and 0.15 in., respectively. The comparison between FIGS. 14A and 14B shows that the permeability results at a constant distance of $d_w$=0.1 in. from the wall provide similar results with respect to the tests performed at the correct distances. In fact, the slope of the linear trend lines of the previously mentioned figures, which are directly related to the permeability, differs of about 9%. On the other hand, tests conducted at a constant distance of $d_w$ 0.15 in. from the wall (FIG. 14C) clearly show a decrease in the correlation factor ($R_2$=0.947 in FIG. 14A compared to the $R_2$=0.657 in FIG. 14C). Additional tests, performed at $d_w$=0.05 in. show completely uncorrelated results ($R_{2<0}$).

Figure 22:
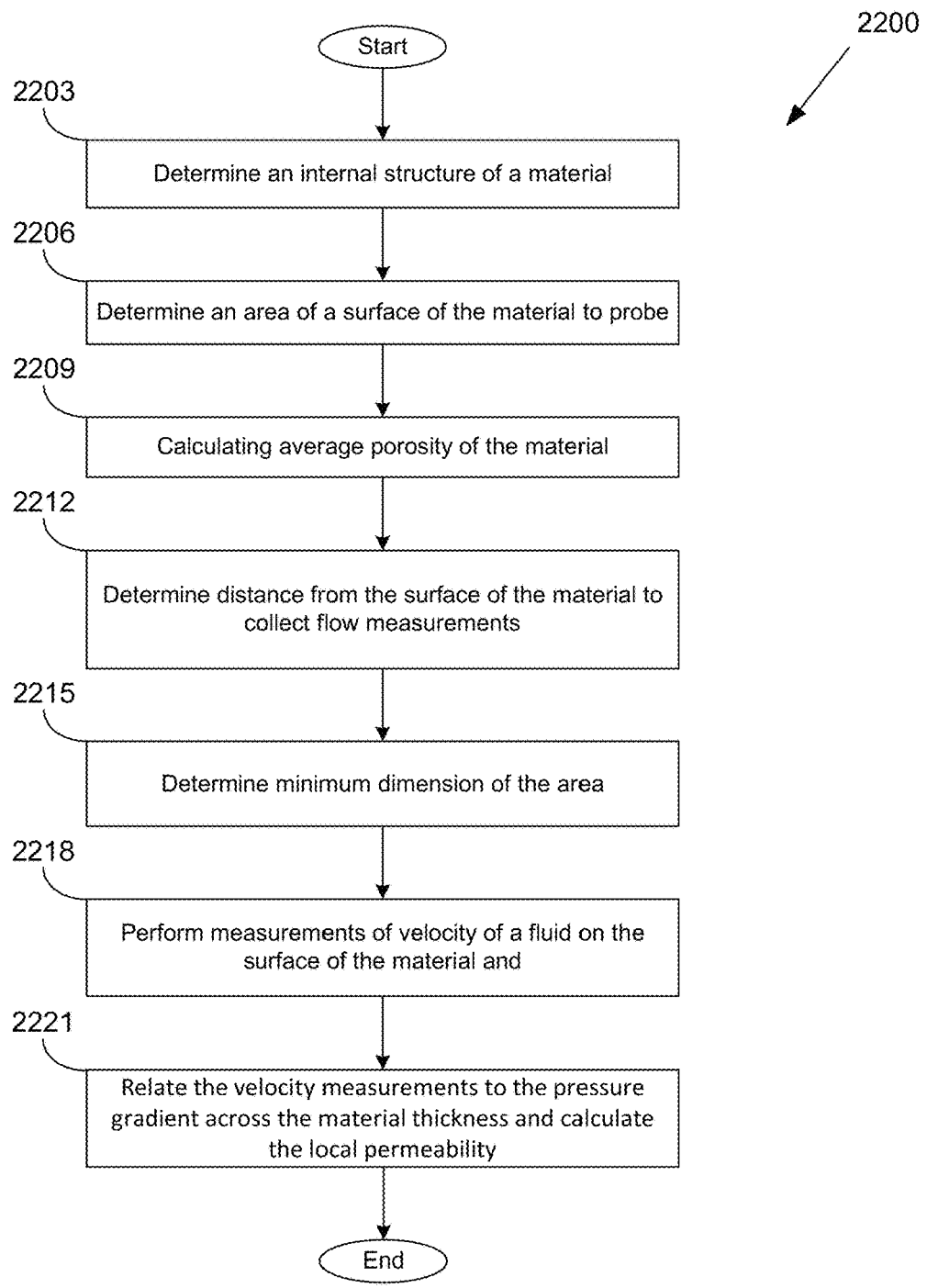
FIG. 22 is a flowchart illustrating one example of functionality implemented as portions of characterization application executed in a computing environment according to various embodiments of the present disclosure.

Referring next to FIG. 22, shown is a flowchart that provides one example of the operation of a portion of a characterization application 2353 according to various embodiments. It is understood that the flowchart of FIG. 22 provides merely an example of the many different types of functional arrangements that may be employed to implement the operation of the portion of the characterization application 2353 as described herein. As an alternative, the flowchart of FIG. 22 may be viewed as depicting an example of elements of a method implemented in the computing device 2300 (FIG. 23) according to one or more embodiments.

At box 2203, the process 2200 involves determining an internal structure of a material. As an example, a CT scan is a non-intrusive technique that can be used to characterize the internal porous lattice of a highly porous carbon-carbon (C—C) structure. The characterization application 2353 can capture a 2D or 3D image of the material to determine the internal structure.

At box 2206, the process 2200 involves determining an area of a surface of the material to probe. The characterization application 2353 can receive an indication of an area to be probed from a user. In some embodiments, a specific size of area is selected by the characterization application 2353 based on a shape and size of the object. In some embodiments, the characterization application 2353 determines a statistical characterization of the internal structure of the material. The characterization application 2353 can determine a range of variations on the surface of the material and the internal structure of the material based on these statistical characterizations. The area of the surface can be selected by performing a statistical analysis of the internal structure of the material. The statistical analysis can be based on the size and distribution of voids in the internal structure.

At box 2209, the process 2200 involves calculating an average porosity of the material. The characterization application 2353 can perform an analysis of an image to determine the porosity of the material or a portion of the material. The characterization application 2353 can calculate the average porosity by averaging the porosity for one or more portions of the material. In some embodiments, the characterization application 2353 can select multiple reference surfaces within the area to be probed.

Each of the reference surfaces can correspond to a portion of the surface of the material. The reference surfaces can differ in size, shape, or size and shape from one another. The characterization application 2353 can calculate an internal porosity by analyzing a 2D image of the surface of the material. The characterization application 2353 can calculate a volumetric porosity by analyzing a 3-D image of the material. The average porosity can be calculated based on the internal porosity, the volumetric porosity, or both.

At box 2212, the process 2200 involves determining a distance from the surface of the material to collect flow measurements. The characterization application 2353 can determine the distance based on an analysis of the structure of the material. The characterization application 2353 can analyze the distribution of internal voids in the internal structure of the material and on a measurement of a velocity of a fluid that is performed by placing the flow measurings device close to the wall.

At box 2215, the process 2200 involves determining a minimum dimension of the area of the surface of the material to be probed. The characterization application 2353 can calculate the minimum dimension based on the average porosity of the area to be probed. The characterization application 2353 can calculate a separate minimum dimension for each reference surfaces within the area. The separate minimum dimensions can each be calculated based on local porosity for each of the reference areas. The characterization application 2353 can calculate an overall minimum dimension for the area to be probed based on the separate minimum dimensions.

In some embodiments, the minimum dimension includes a distance to move in each of the two-dimensions parallel to the surface. As an example, the minimum dimension can include a first distance in a first dimension parallel to the surface of the material and a second distance in a second dimension parallel to the surface of the material and perpendicular to the first dimension. In other embodiments, the minimum dimension is an absolute distance to move between measurements without reference to direction.

At box 2218, the process 2200 involves performing measurements of a velocity of fluid on the surface of the material. The measurements can be performed with a probe positioned perpendicular from the surface of the material at the distance determined in box 2212. A control system can be configured to adjust the position of the probe in three dimensions. The control system can be any one of the systems shown in FIGS. 5A and 5B, among other known systems. The control system can include a fluid flow measuring device, such as, for example, a calibrated anemometer.

The characterization application 2353 can adjust the position so that the probe is the set distance from the surface. Between each measurement, the characterization application 2353 can move the probe in the two-dimensions parallel to the surface of the material. Each movement can be at least the minimum dimension as determined in box 2215. The characterization application 2353 can move the probe the minimum dimension between each measurement.

The measurements can be taken with respect to gradient pressure across the thickness of the material. The characterization application 2353 can measure a permeability of the material based on the measurements of the velocity of the fluid on the surface of the material at the distance.

At box 2221, the process 2200 involves relating the velocity measurements to the pressure gradient across the material thickness and calculating the local permeability. The characterization application 2353 can process the velocity measurements and relate the velocity measurements to the pressure gradient, such as, for example, across the thickness of the material. The characterization application 2353 can calculate the local permeability of the material based on the relation of velocity to pressure gradient across the material thickness.

Figure 23:
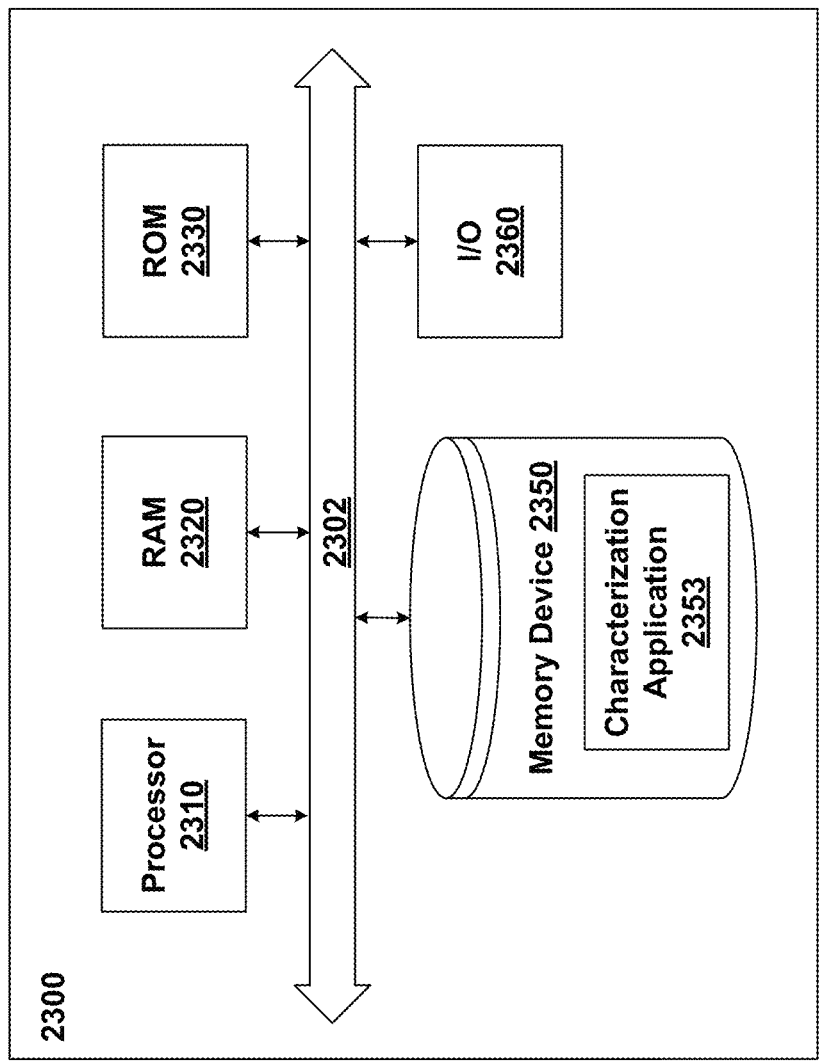
FIG. 23 is a schematic block diagram that provides one example illustration of a computing environment according to various embodiments of the present disclosure.

With reference to FIG. 23, shown is a schematic block diagram of a computing device 2300 in a computing environment according to an embodiment of the present disclosure. A computing environment can include one or more computing devices 2300. Each computing device 2300 includes at least one processor circuit, for example, having a processor 2310 and a memory 2320 or 2350, both of which are coupled to a local interface 2302. To this end, each computing device 2300 may comprise, for example, at least one server computer or like device. The local interface 2302 may comprise, for example, a data bus with an accompanying address/control bus or other bus structure as can be appreciated.

Stored in the memory 2320 or 2350 are both data and several components that are executable by the processor 2310. In particular, stored in the memory 2320 or 2350 and executable by the processor 2310 is the characterization application 2353, and potentially other applications. Also stored in the memory 2320 or 2350 may be a data store 2350 and other data. In addition, an operating system may be stored in the memory 2320 or 2350 and executable by the processor 2310.

It is understood that there may be other applications that are stored in the memory 2320 or 2350 and are executable by the processor 2310 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 2320 or 2350 and are executable by the processor 2310. In this respect, the term "executable" means a program file that is in a form that can ultimately be run by the processor 2310. Examples of executable programs may be, for example, a compiled program that can be translated into machine code in a format that can be loaded into a random access portion of the memory 2320 or 2350 and run by the processor 2310, source code that may be expressed in proper format such as object code that is capable of being loaded into a random access portion of the memory 2320 or 2350 and executed by the processor 2310, or source code that may be interpreted by another executable program to generate instructions in a random access portion of the memory 2320 or 2350 to be executed by the processor 2310, etc. An executable program may be stored in any portion or component of the memory 2320 or 2350 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 2320 or 2350 is defined herein as including both volatile and nonvolatile memory and data storage components. Volatile components are those that do not retain data values upon loss of power. Nonvolatile components are those that retain data upon a loss of power. Thus, the memory 2320 or 2350 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 2310 may represent multiple processors 2310 and/or multiple processor cores and the memory 2320 or 2350 may represent multiple memories 2320 or 2350 that operate in parallel processing circuits, respectively. In such a case, the local interface 2302 may be an appropriate network that facilitates communication between any two of the multiple processors 2310, between any processor 2310 and any of the memories 2320 or 2350, or between any two of the memories 2320 or 2350, etc. The local interface 2302 may comprise additional systems designed to coordinate this communication, including, for example, performing load balancing. The processor 2310 may be of electrical or of some other available construction.

Although characterization application 2353, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowchart of FIG. 22 show the functionality and operation of an implementation of portions of the characterization application 2353. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 2310 in a computer system or other system. The machine code may be converted from the source code, etc. If embodied in hardware, each block may represent a circuit or a number of interconnected circuits to implement the specified logical function(s).

Although the flowchart of FIG. 22 shows a specific order of execution, it is understood that the order of execution may differ from that which is depicted. For example, the order of execution of two or more blocks may be scrambled relative to the order shown. Also, two or more blocks shown in succession in FIG. 22 may be executed concurrently or with partial concurrence. Further, in some embodiments, one or more of the blocks shown in FIG. 22 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including characterization application 2353, that comprises software or code can be embodied in any non-transitory computer-readable medium for use by or in connection with an instruction execution system such as, for example, a processor 2310 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including characterization application 2353, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 2300 or in multiple computing devices in the same computing environment. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A system, comprising:
    a probe positioned perpendicular to a surface of a material, the probe configured to sense a velocity of a fluid;
    a control system configured to adjust a distance away from the surface of the material and to adjust a position of the probe parallel to the material; and
    the control system being further configured to move the probe to be a specific distance from the surface of the material and to move the probe from a first position to a second position by moving the probe a minimum dimension parallel to the surface of the material, the minimum dimension being based at least in part on the surface of the material and an internal structure of the material, wherein the probe is configured to perform a measurement of the velocity of the fluid at the first position and the second position.

2. The system of claim 1, wherein the control system comprises a computing device configured to at least:
    capture an image of a portion of the surface and the internal structure of the material;
    perform an analysis of the image to determine a porosity of the portion of the surface and the internal structure of the material; and determine an average porosity based at least in part on the porosity of the portion of the material, wherein the minimum dimension is based at least in part on the average porosity.

3. The system of claim 1, wherein the control system comprises a computing device configured to at least:
   determine a statistical characterization of an internal structure of the material;
   determine a range of variations of the surface of the material to probe based at least in part on the statistical characterization; and
   determine an area of the surface of the material to probe based at least in part on the range of variations of the surface.

4. The system of claim 3, wherein the computing device is further configured to at least determine the specific distance based at least in part on an analysis of a distribution of internal voids in the internal structure of the material.

5. The system of claim 1, wherein the control system is further configured to determine correlations of the velocity to a gradient for the first position and the second position.

6. The system of claim 1, wherein the control system is further configured to determine a local permeability of the material at the first position based at least in part on the velocity at the first position.

7. The system of claim 1, wherein the control system is further configured to move the probe from the second position to a third position by moving the probe parallel to the surface of the material and the probe is further configured to perform another measurement of the velocity of the fluid at the third position.

8. A method for permeability measurements of a material comprising:
   determining a distance from a surface of the material to collect flow measurements for an area of the surface of the material;
   determining a minimum dimension of the area of the surface of the material to be probed; and
   performing a statistical analysis of the material by determining a plurality of correlations of mass-flux to pressure gradient at a plurality of locations of interest for permeability measurements, the plurality of locations of interest being based at least in part on the distance and the minimum dimension, wherein a fluid flow measuring device performs a measurement of a velocity of a fluid at a first location of the plurality of locations and a second location of the plurality of locations, the first location and the second location being separated by the minimum dimension.

9. The method of claim 8, wherein the distance from the surface is determined based at least in part on an analysis of a distribution of internal voids in a structure of the material.

10. The method of claim 8, further comprising:
    determining an internal structure of the material using a non-intrusive technique; and
    determining the area of the surface of the material to probe by performing another statistical analysis of the internal structure of the material based at least in part on a size and distribution of a plurality of voids in the internal structure.

11. The method of claim 8, wherein determining the minimum dimension of the area of the surface further comprises:
    obtaining an internal structure of the material by using non-intrusive techniques;
    calculating an average porosity of the material by using a plurality of reference surfaces, at least one of the plurality of reference surfaces differing in at least one of: a size or a shape; and
    obtaining a plurality of minimum dimensions individually corresponding to the plurality of reference surfaces, wherein the minimum dimension is determined based at least in part on the plurality of minimum dimensions.

12. The method of claim 11, wherein the average porosity is calculated based at least in part on at least one of an internal porosity or a volumetric porosity, wherein the internal porosity is calculated by analyzing at least one 2-D image of the surface of the material and the volumetric porosity is calculated by analyzing a 3-D image of the surface of the material.

13. The method of claim 8, further comprising determining a plurality of measurements of the velocity of the fluid on the surface of the material at the distance using the fluid flow measuring device, wherein the plurality of measurements of the velocity are taken with respect to a gradient pressure across a thickness of the material, the plurality of measurements comprising the measurement taken at the first location and the second location.

14. The method of claim 13, further comprising, wherein the fluid flow measuring device is a calibrated anemometer.

15. The method of claim 8, wherein the minimum dimension comprises an absolute distance.

16. A method for permeability measurements of a material comprising:
    identifying an area of a surface of the material to be analyzed;
    calculating an average porosity of the material by using a plurality of reference surfaces;
    determining a minimum dimension between measurements of the surface based at least in part on the average porosity of the area of the surface;
    performing a first measurement of a plurality of measurements at a first location and a second measurement of the plurality of measurements at a second location, wherein the first location and the second location are the minimum dimension apart; and
    measuring a permeability of the material based at least in part on the plurality of measurements of a velocity of a fluid on the surface of the material at a distance.

17. The method of claim 16, further comprising determining the distance from the surface of the material to collect measurements for the area based at least in part on an analysis of a distribution of internal voids in a structure of the material.

18. The method of claim 16, wherein the minimum dimension comprises a first distance in a first dimension parallel to the surface of the material and a second distance in a second dimension parallel to the surface of the material and perpendicular to the first dimension.

19. The method of claim 16, further comprising determining the plurality of reference surfaces, each of the plurality of reference surfaces corresponding to a subsection of the area of the surface of the material, wherein the minimum dimension between the measurements is further based at least in part on a respective minimum dimension corresponding to individual ones of the plurality of reference surfaces.

20. The method of claim 16, further comprising:
    moving a probe to be a specific distance from the surface of the material to be analyzed; and subsequent to the first measurement and prior to the second measurement, moving the probe from the first location to the second location.

* * * * *